US009248023B2

(12) United States Patent
Ries et al.

(10) Patent No.: US 9,248,023 B2
(45) Date of Patent: Feb. 2, 2016

(54) ILIAC CANAL PROSTHESIS

(75) Inventors: Michael D. Ries, Tiburon, CA (US);
Jeffrey Joel Shea, Memphis, TN (US);
David C. Kelman, Collierville, TN
(US); Jeffrey A. Sharp, Salt Lake City,
UT (US)

(73) Assignee: Smith & Nephew, Inc., Memphis, TN (US)

( * ) Notice: Subject to any disclaimer, the term of this patent is extended or adjusted under 35 U.S.C. 154(b) by 285 days.

(21) Appl. No.: 13/132,280

(22) PCT Filed: Dec. 2, 2009

(86) PCT No.: PCT/US2009/066457
§ 371 (c)(1),
(2), (4) Date: Aug. 12, 2011

(87) PCT Pub. No.: WO2010/065672
PCT Pub. Date: Jun. 10, 2010

(65) Prior Publication Data
US 2011/0288650 A1    Nov. 24, 2011

Related U.S. Application Data

(60) Provisional application No. 61/119,210, filed on Dec. 2, 2008.

(51) Int. Cl.
*A61F 2/34* (2006.01)
*A61F 2/30* (2006.01)
(Continued)

(52) U.S. Cl.
CPC .............. *A61F 2/34* (2013.01); *A61B 17/1659* (2013.01); *A61B 17/1664* (2013.01);
(Continued)

(58) Field of Classification Search
CPC .............. A61F 2/34; A61F 2220/0025; A61F 2002/3401; A61F 2002/30538; A61F 2250/0006; A61F 2002/3448; A61F 2/30734
USPC ........................................... 623/22.32, 22.38
See application file for complete search history.

(56) References Cited

U.S. PATENT DOCUMENTS 4,936,856 A    6/1990  Keller
5,376,125 A   12/1994  Winkler
(Continued)

FOREIGN PATENT DOCUMENTS

CN       1230391 A    10/1999
JP       3325889       9/2002
(Continued)

OTHER PUBLICATIONS

Australian Examination Report No. 1; Australian Patent Office; Australian Paptent Application No. 2009322396; Dec. 15, 2014; 3 pages.
(Continued)

*Primary Examiner* — Bruce E Snow
*Assistant Examiner* — Melissa Hoban
(74) *Attorney, Agent, or Firm* — Taft Stettinus & Hollister LLP

(57) ABSTRACT

An acetabular prosthetic device for implantation in an iliac canal and acetabulum of an ilium comprises a stem and an acetabular component. The stem may be configured to be implanted in the iliac canal. The acetabular component may be configured to be implanted in the acetabulum and fixed to the stem. The acetabular component may further comprise a connection portion to adjustably connect the acetabular component to the stem such that the acetabular component is configured to be oriented in a plurality of orientations before being fixed to the stem.

28 Claims, 21 Drawing Sheets

(51) Int. Cl.
*A61B 17/16* (2006.01)
*A61B 17/86* (2006.01)
*A61F 2/28* (2006.01)
*A61B 17/88* (2006.01)

(52) U.S. Cl.
CPC ........ *A61F 2/30721* (2013.01); *A61F 2/30734* (2013.01); *A61F 2/30749* (2013.01); *A61B 17/86* (2013.01); *A61B 17/8897* (2013.01); *A61F 2/28* (2013.01); *A61F 2002/285* (2013.01); *A61F 2002/3078* (2013.01); *A61F 2002/3085* (2013.01); *A61F 2002/3092* (2013.01); *A61F 2002/30332* (2013.01); *A61F 2002/30433* (2013.01); *A61F 2002/30449* (2013.01); *A61F 2002/30507* (2013.01); *A61F 2002/30538* (2013.01); *A61F 2002/30604* (2013.01); *A61F 2002/30736* (2013.01); *A61F 2002/30841* (2013.01); *A61F 2002/30878* (2013.01); *A61F 2220/005* (2013.01); *A61F 2220/0025* (2013.01); *A61F 2220/0033* (2013.01); *A61F 2220/0041* (2013.01); *A61F 2250/0006* (2013.01)

(56) References Cited

U.S. PATENT DOCUMENTS

| | | | |
|---|---|---|---|
| 5,733,338 A * | 3/1998 | Kampner | 128/898 |
| 5,879,353 A | 3/1999 | Terry | |
| 5,916,268 A | 6/1999 | Schollner et al. | |
| 6,045,583 A * | 4/2000 | Gross et al. | 623/22.21 |
| 6,106,536 A | 8/2000 | Lechot | |
| 6,228,121 B1 * | 5/2001 | Khalili | 623/22.36 |
| 6,319,256 B1 | 11/2001 | Spotorno et al. | |
| 6,368,324 B1 | 4/2002 | Dinger et al. | |
| 6,997,928 B1 | 2/2006 | Penenberg | |
| 2001/0027346 A1 | 10/2001 | Keller | |
| 2004/0117029 A1 * | 6/2004 | Lewis et al. | 623/22.28 |
| 2004/0254646 A1 * | 12/2004 | Stone et al. | 623/23.15 |
| 2005/0021148 A1 | 1/2005 | Gibbs | |
| 2005/0187637 A1 | 8/2005 | Karrer et al. | |
| 2006/0129159 A1 | 6/2006 | Lee | |
| 2008/0021568 A1 * | 1/2008 | Tulkis et al. | 623/22.35 |
| 2008/0046091 A1 * | 2/2008 | Weiss et al. | 623/22.37 |
| 2008/0195221 A1 | 8/2008 | Howald et al. | |
| 2009/0088865 A1 | 4/2009 | Brehm | |
| 2010/0262144 A1 * | 10/2010 | Kelman et al. | 606/62 |

FOREIGN PATENT DOCUMENTS

| | | |
|---|---|---|
| JP | 4180506 | 11/2008 |
| JP | 2009-534062 | 9/2009 |
| RU | 2164102 C1 | 3/2001 |
| RU | 2259178 C2 | 8/2005 |
| WO | WO 03/002022 A1 | 1/2003 |
| WO | WO 2005/060876 A1 | 7/2005 |

OTHER PUBLICATIONS

European Examination Report; European Patent Office; European Patent Application No. 09 831 075.8; Jun. 24, 2014; 5 pages.
Australian Examination Report No. 1; Australian Patent Office; Australian Patent Application No. 2009322391; Sep. 19, 2014; 4 pages.
Japanese Office Action; Japanese Patent Office; Japanes Patent Application No. 2011-539667; Oct. 14, 2014; 4 pages.
Chinese Search Report; Chinese Patent Application No. 200980156364.6; Jun. 7, 2013; 5 pages.
Chinese First Office Action; Chinese Patent Application No. 200980156364.6; Jun. 20, 2013; 8 pages.
Chinese Supplemental Search Report; Chinese Patent Application No. 200980156364.6; Apr. 3, 2014; 4 pages.
Chineses Second Office Action; Chinese Patent Application No. 200980156364.6; Apr. 15, 2014; 6 pages.
Chinese Third Office Action; Chinese Patent Application No. 200980156364.6; Dec. 22, 2014; 3 pages.
Russian Office Action; Russian Patent Office; Russian Patent Application No. 2011126293; Feb. 12, 2014; 6 pages.
James E. Bateman/V. Danilyaka; Standard Surgery Technology for Bipolar Arthroplasty; Margo Anterior; 2005; No. 3; pp. 1-8.

* cited by examiner

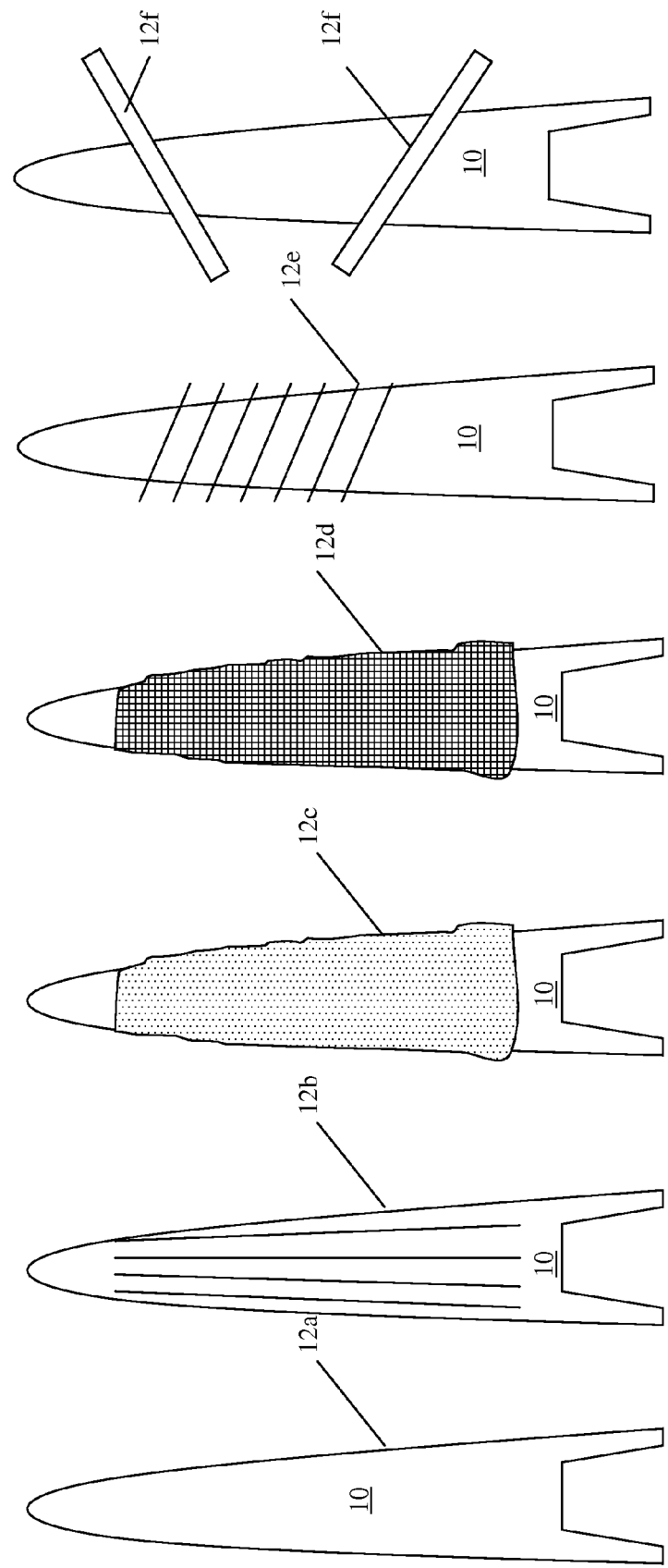

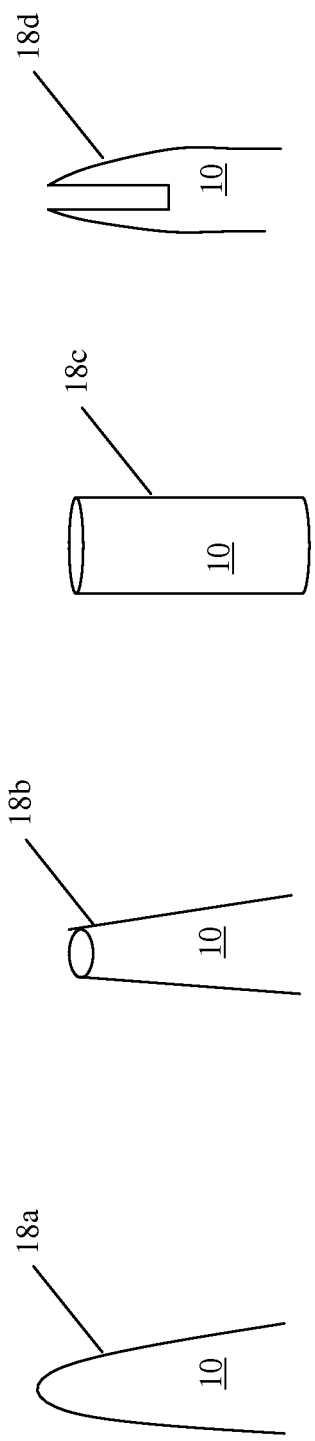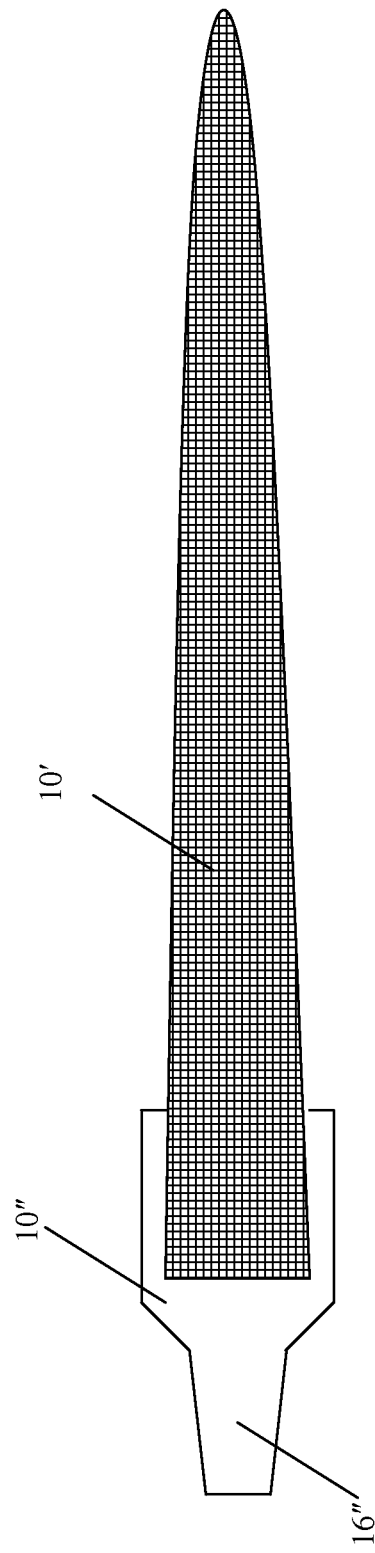

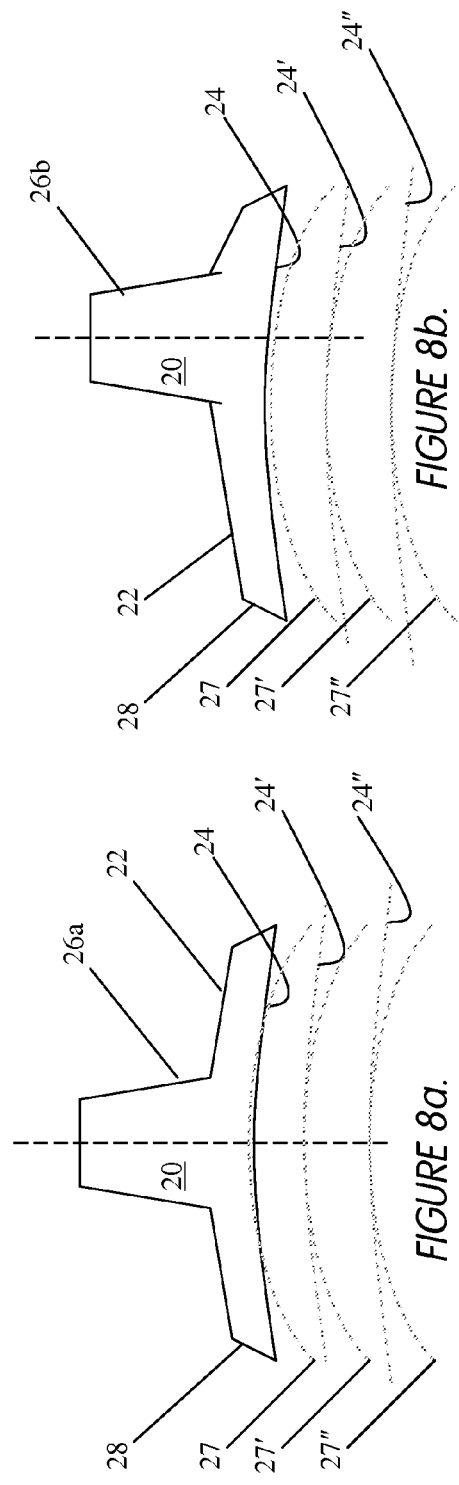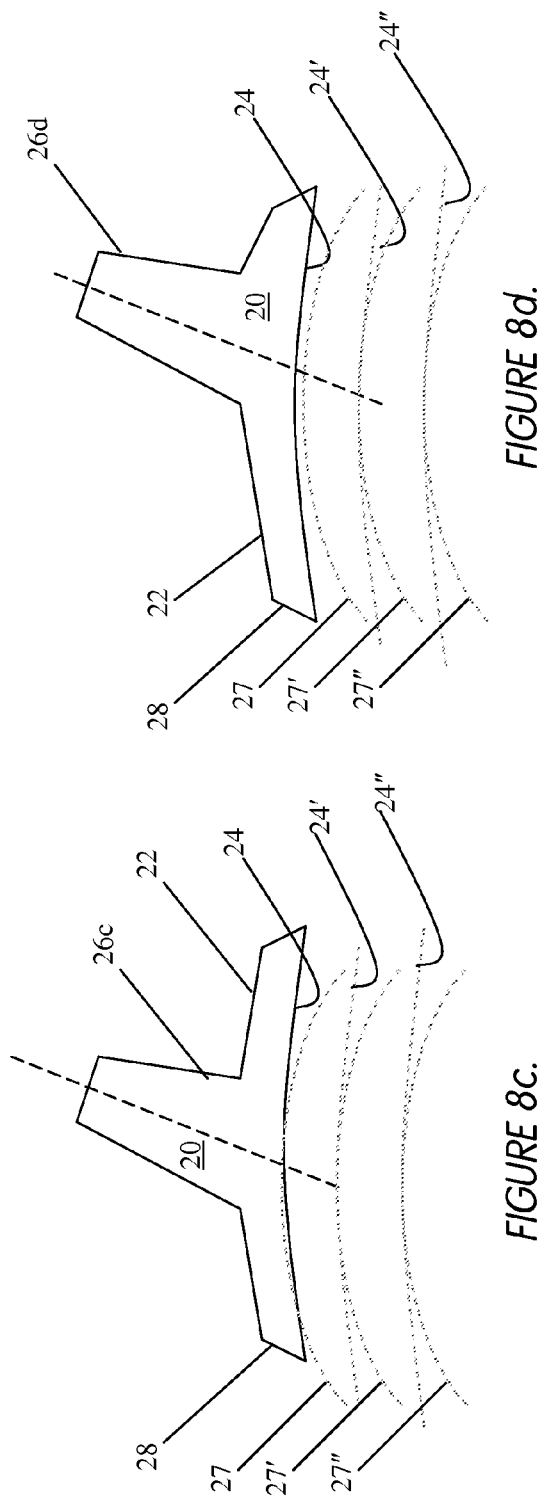
FIGURE 8a.
FIGURE 8b.
FIGURE 8c.
FIGURE 8d.

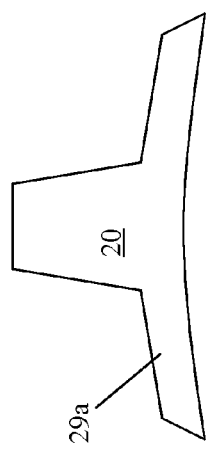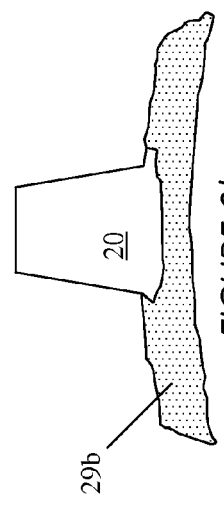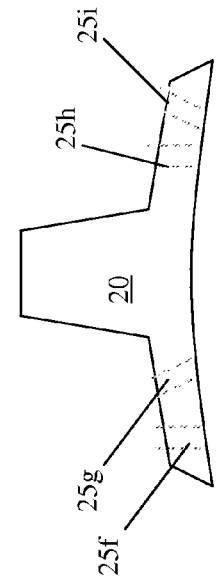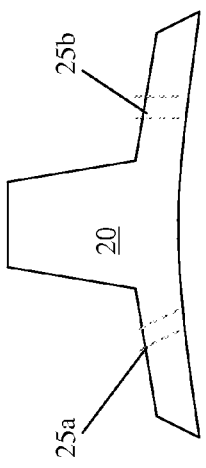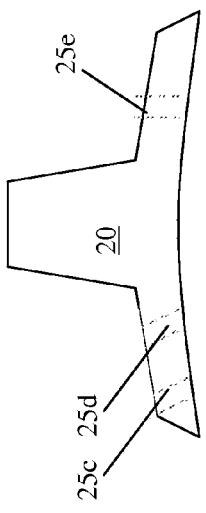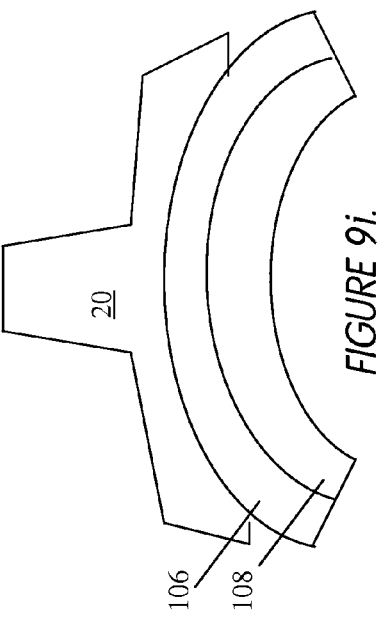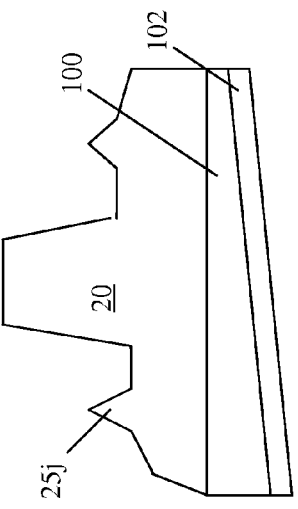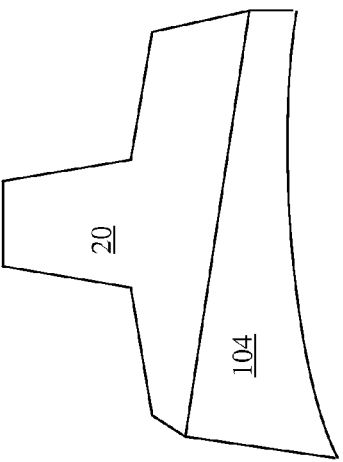

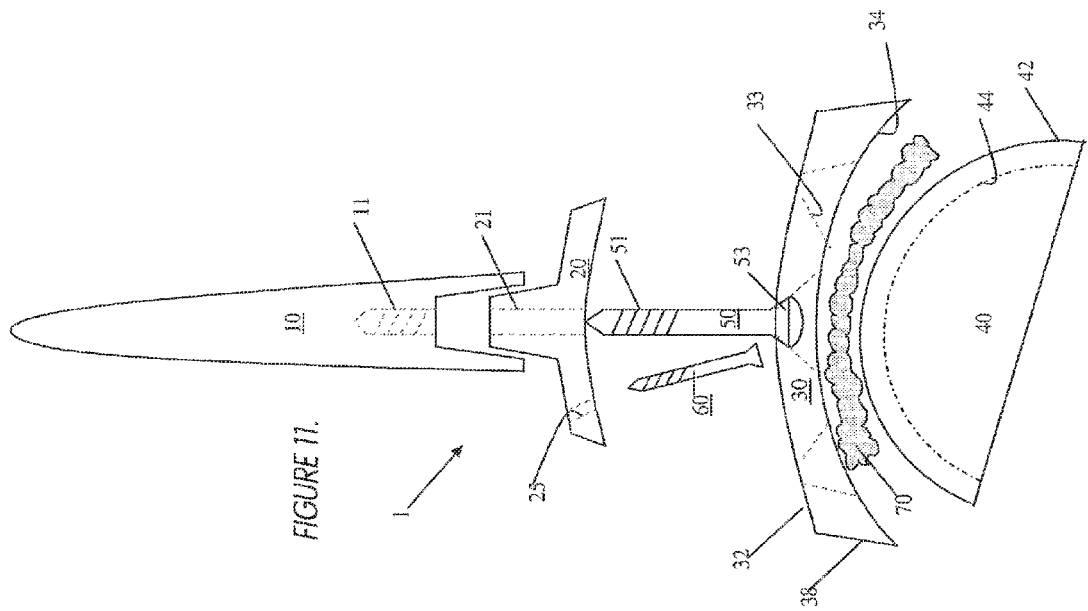
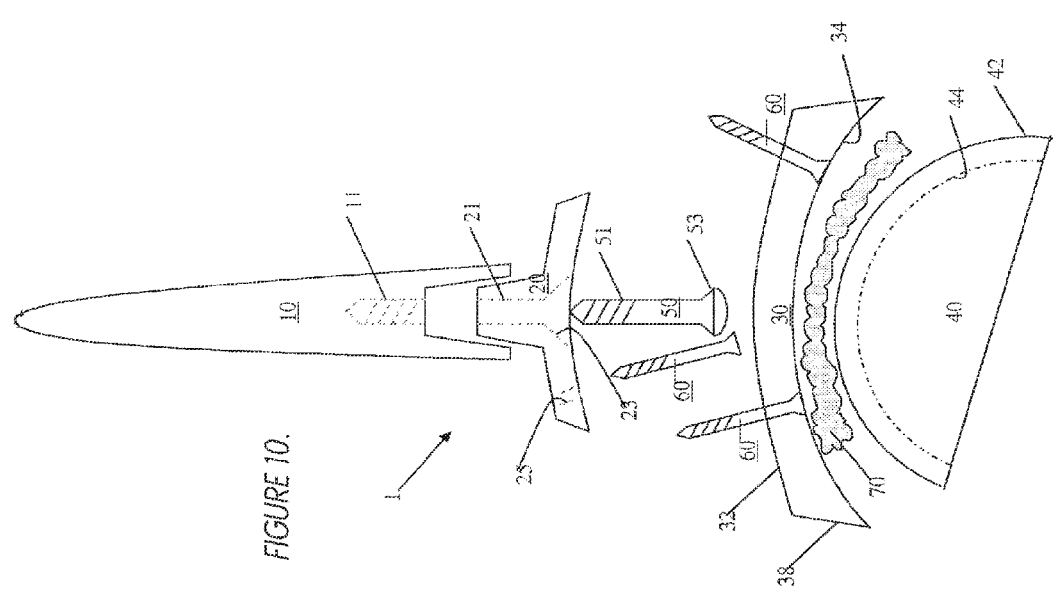

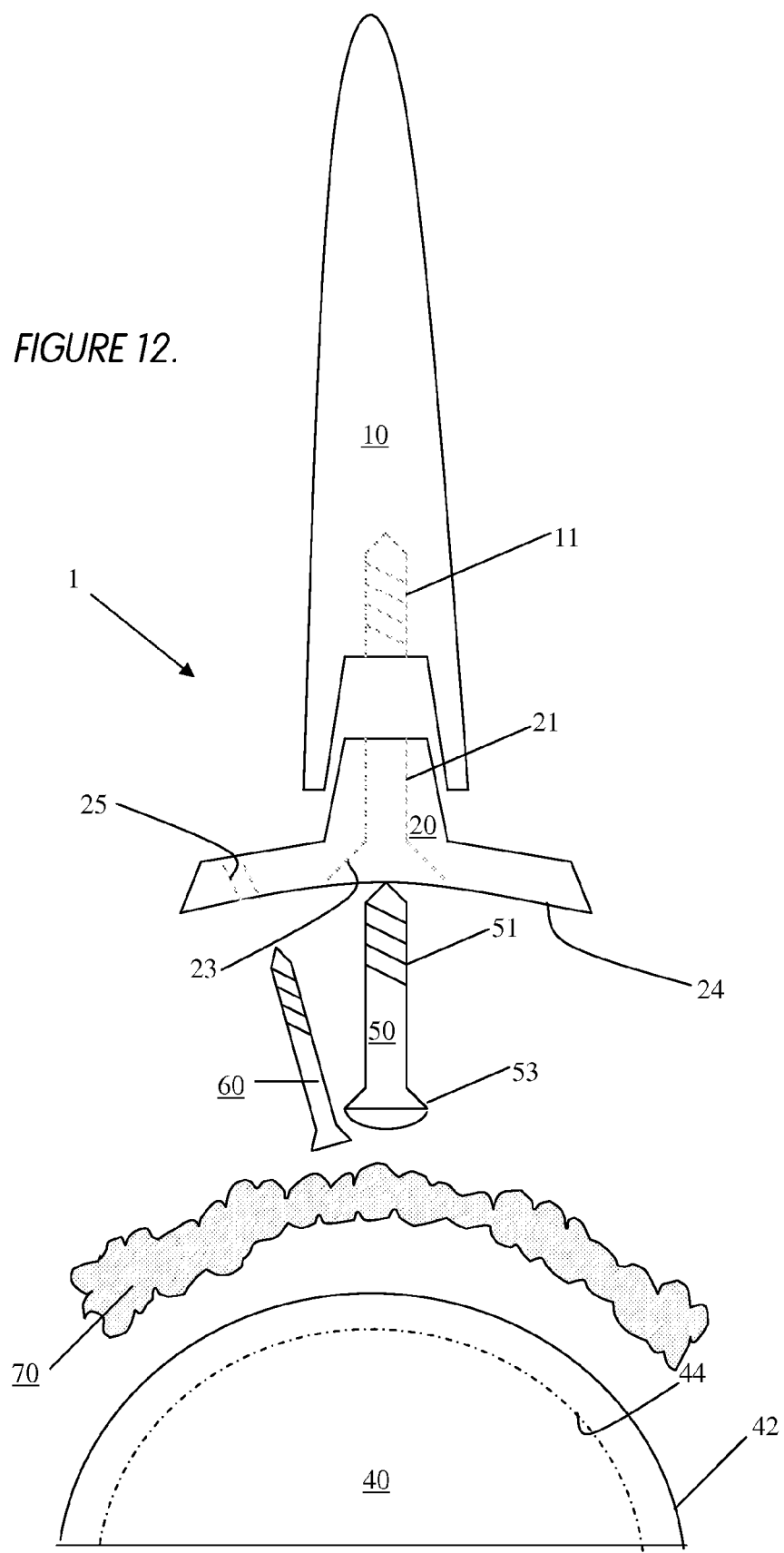

ILIAC CANAL PROSTHESIS

CROSS-REFERENCE TO RELATED APPLICATIONS

This application is a United States National Phase filing of International Application No. PCT/US2009/066457 filed Dec. 2, 2009, which claims the benefit of U.S. Provisional Application No. 61/119,210, filed Dec. 2, 2008 and titled "Iliac Canal Prosthesis". The disclosure of these applications are incorporated by reference in their entirety.

BACKGROUND OF THE INVENTION

1. Field of the Invention

The present invention relates generally to methods of securing acetabular implants, and more particularly to an apparatus and method of securing acetabular augments alone, or in combination with an acetabular shell, to a hip using the canal of the ilium.

2. Related Art

In the past, the iliac canal has been utilized for fixedly securing an artificial acetabular bearing surface to pelvic bone. FIG. 1 illustrates one example of such a prior art device. Shown in FIG. 1, is an all-metal Ring prosthesis device (900) which is configured for mounting within the iliac canal. Device (900) typically comprises a shank (901) having threads (902) thereon, a shaft base (903), a transition area (904), and a bearing cup (905) having an inner bearing surface (907) and a rim (906). Typically, device (900) is constructed as one, homogeneous, monolithic, metal piece, which leaves no adjustability or material options to a surgeon. Moreover, once the shank (901) of the device (900) is secured into the iliac canal, the orientations of the bearing cup (905), the rim (906), and the bearing surface (907) relative to the ilium or acetabulum is fixed concentrically with the shank (901). Therefore, fixation of the device (900) may come at the expense of not providing the optimum head coverage necessary for stability throughout a range of motion.

FIGS. 2a-2d illustrate the method steps of installing said Ring prosthesis device (900). First, a canal guide (922) that is mounted on a base (920) is inserted into the acetabulum. The canal guide (922) is inserted into the intramedullary canal of the ilium (i.e., the "iliac canal") and is then left inside the iliac canal. Second, a cannulated reamer (924) slides over the canal guide (922) and reams out the iliac canal. The canal guide (922) and reamer (924) are then removed from the iliac canal. Thirdly, a frustoconical reamer (926) having a cutting edge (928) bores out a frustoconical countersunk recess in the acetabulum. The countersunk recess provides a clearance for the transition area (904) and the bearing cup (905). Lastly, the Ring prosthesis device (900) is inserted into and secured within the iliac canal by screwing the device (900) into the iliac canal. Torque engagement means (930) is provided on or adjacent to the exposed rim (906).

FIGS. 3a and 3b illustrate another example of a prior art Ring prosthesis (950) called an uncemented polyethylene-on-metal (UPM) hip prosthesis. The UPM hip prosthesis (950) is a successor to the all-metal Ring prosthesis (900) shown in FIG. 1, and similarly utilizes the iliac canal for fixedly securing an acetabular bearing surface to pelvic bone. The prosthesis (950) includes a frustoconical portion (954) which connects a bearing cup (956). The bearing cup (956) has a generally hemi-spherical bearing surface (955), and the frustoconical portion (954) has an eccentric or offset shaft (952) having protuberances thereon. A metallic ring (953) is centered within a groove (957) to allow the rim of the bearing cup (956) to be visible on radiographs.

Prostheses (950) such as the one shown in FIGS. 3a and 3b are typically formed from a monolithic block of ultra-high-molecular-weight polyethylene and may generally be described as an offset conical cup having a finned intraosseous peg mounted thereon. Since the UPM prosthesis (950) is eccentric, it relies on a wedge press-fit into an accurately reamed acetabulum, rather than concentric screwing into the iliac canal.

The eccentric frustoconical portion (954) serves to prevent rotation and to allow small amounts of version adjustment for better head coverage and stability. Grooves extending along the longitudinal axis of the frustoconical portion (954) give additional rotational stability. The prosthesis (950) is fitted into a reamed track created through the centre of the iliopubic buttress and the cup is punched into position. Acetabular prostheses (950) shown in FIGS. 3a and 3b are generally used in combination with either a Ring or a Norwich-type of uncemented femoral component.

FIG. 26 illustrates some examples of prior art Trabecular Metal™ acetabular augments (1000, 1002, 1004, 1006) provided by Zimmer, Inc. The augments are composed of porous tantalum and are intended to fill large bone voids during revision hip arthroplasty surgery, so that acetabular cup stability can be achieved (acetabular cup not shown). These prior art augments do not have protrusion portions configured for insertion into the IM canal of the ilium. The augments also lack a means for mounting the augment to the IM canal of the ilium. Even if a screw (not shown) was to be inserted through one of the holes (1020) provided on some of the augments (1000, 1002, 1004) and into the IM canal of the ilium according to the teachings presented herein, the augments would not seat correctly within the acetabulum, would become unstable, and would not function as intended. Lastly, these prior art augments (1000, 1002, 1004, 1006) are not designed or intended to be modular, interchangeable, interconnectable, and adjustable as are the augments of the present invention.

To this end, all current acetabular prostheses utilizing the iliac canal for fixation do not provide a surgeon with modularity, intraoperative options, and/or material choices. Additionally, all conventional augments designed to fill large bone voids do not provide a surgeon with the option to use the iliac canal as a means for providing prosthesis support and indicating proper orientation in severe cases.

Moreover, the prior art acetabular prostheses (900, 950) described above have been designed for and used only for primary hip surgeries (i.e., first hip surgery). That is, such prior art devices utilizing the iliac canal for fixation are not intended to address the many special circumstances, substantial bone losses, poor bone quality, and other challenges that face a surgeon during complex revision hip surgeries (i.e., surgeries after a first hip surgery).

SUMMARY OF THE INVENTION

The aforementioned needs are satisfied by several aspects of the present invention.

According to one aspect of the invention, there is provided a method of providing an acetabular implant adapted for use in revision hip surgery. The implant comprises a stem portion configured for securement within the iliac canal, a shell portion, and a means for adjustably mounting said shell portion to said stem portion.

According to another aspect of the invention, there is provided a method of implanting an acetabular implant adapted for use in revision hip surgery. The method includes the steps of: finding the iliac canal, reaming the iliac canal, inserting a stem portion into the prepared iliac canal, and securing a shell portion to the stem portion using a means for adjustably mounting.

According to yet another aspect, an acetabular prosthetic device for implantation in an iliac canal and acetabulum of an ilium comprises a stem and an acetabular component. The stem may be configured to be implanted in the iliac canal. The acetabular component may be configured to be implanted in the acetabulum and fixed to the stem. The acetabular component may further comprise a connection portion to adjustably connect the acetabular component to the stem such that the acetabular component is configured to be oriented in a plurality of orientations before being fixed to the stem.

Yet another aspect of the invention provides the connection portion may be an augment. The augment may be configured to be received between the stem and the acetabular component. A first surface of the augment may be configured to orient the augment with respect to the stem and a second surface of the augment may be configured to orient the acetabular component with respect to the stem.

According to another aspect, a plurality of augments are provided. Each of the plurality of augments may have a first surface configured to orient the augment with respect to the stem and a second surface of the augment configured to orient the acetabular component with respect to the stem such that each of the plurality of augments orients the acetabular component in a different orientation from at least one other of the plurality of augments.

According to yet another aspect, the connection portion may be a positioning portion within the acetabular component.

The connection portion may be a slot within the acetabular component according to another aspect. The slot may have a plurality of positions through which a fixation element may secure the acetabular component to the stem.

According to another aspect, the fixation element may be a screw.

According to yet another aspect, the acetabular device may be an acetabular shell.

Yet another aspect may provide a second augment configured to be received between the augment and the acetabular component such that the second augment fills a bone void between the augment and the acetabular component.

According to another aspect, the augment and the stem are fixed together through a taper lock.

According to yet another aspect, the augment further comprises bone fixation elements to fix the augment to bone.

Yet another aspect may provide a spike as the bone fixation element.

Another aspect provide for a method of implanting an acetabular prosthetic device in an acetabulum. The method reams an iliac canal. Another step fixes a stem within the iliac canal. Another step adjustably positions an acetabular component within the acetabulum to determine a proper orientation of the acetabular component The acetabular component may be fixed to the stem.

According to another aspect, athe step of locating the iliac canal may be performed with a canal guide.

According to yet another aspect, the reaming step comprises reaming the iliac canal by advancing a reamer over the canal guide.

Yet another aspect may provide for the adjustably positioning step to comprise placing an augment between the stem and the acetabular component. A first surface of the augment may be configured to orient the augment with respect to the stem and a second surface of the augment may be configured to orient the acetabular component with respect to the stem.

According to another aspect, the adjustably positioning step may further comprise choosing an augment from a plurality of augments. Each of the plurality of augments may have a first surface configured to orient the augment with respect to the stem and a second surface of the augment configured to orient the acetabular component with respect to the stem such that each of the plurality of augments orients the acetabular component in a different orientation from at least one other of the plurality of augments.

Yet another aspect may comprise the step of fixing the augment to bone.

According to another aspect, the augment may be configured with bone spikes.

According to yet another aspect, the adjustably positioning step may further comprise orienting a positioning portion of the acetabular component over the stem and fixing the acetabular component to the stem.

According to another aspect, the fixing the acetabular component to the stem step may comprise screwing the acetabular component to the stem.

Further areas of applicability of the present invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIGS. 5a-f depict stem portions according to some embodiments of the present invention.

FIGS. 6a-d illustrate stem portion ends according to some embodiments of the present invention;

FIG. 7 is a side view of a porous stem portion according to some embodiments of the present invention;

FIG. 8a-d illustrate stem augments having different eccentricities and offsets according to some embodiments of the present invention;

FIGS. 9a-f illustrate stem augment configurations according to some embodiments of the present invention;

FIGS. 9g-i illustrate stem augments in combination with wedges, spacers, and other augments according to some embodiments of the present invention.

FIG. 10 shows a cemented acetabular prosthesis according to some embodiments of the present invention;

FIG. 11 shows a cemented acetabular prosthesis according to some other embodiments of the present invention;

FIG. 12 shows a cemented acetabular prosthesis according to other embodiments of the present invention;

DETAILED DESCRIPTION OF THE EMBODIMENTS

The following description of the preferred embodiments is merely exemplary in nature and is in no way intended to limit the invention, its application, or uses.

The invention provides, in part, a method of reconstructing an acetabular region utilizing the iliac canal as a stable anchor and as a means for indicating proper orientation. Occasionally, a patient's acetabular region may be compromised to the point that it is not recognizable. Methods of the present invention utilize the iliac canal as an intact, repeatably findable, easy to locate anatomical landmark which can be used as an anchor support and as a means to orient and mount an acetabular shell with a relatively high degree of confidence, even in severe trauma or revision cases. A stem portion is inserted into the iliac canal, essentially forming a "foundation" for building up lost or compromised bone. A series of wedges, spacers, and augments may be used to build up said lost or compromised bone and to provide to an acetabular shell, an improved means for fixation in situations that would otherwise yield poor fixation and initial stability.

It is preferred that cementless options be utilized, however, acetabular implants of the present invention may incorporate cemented options.

Figure 1:
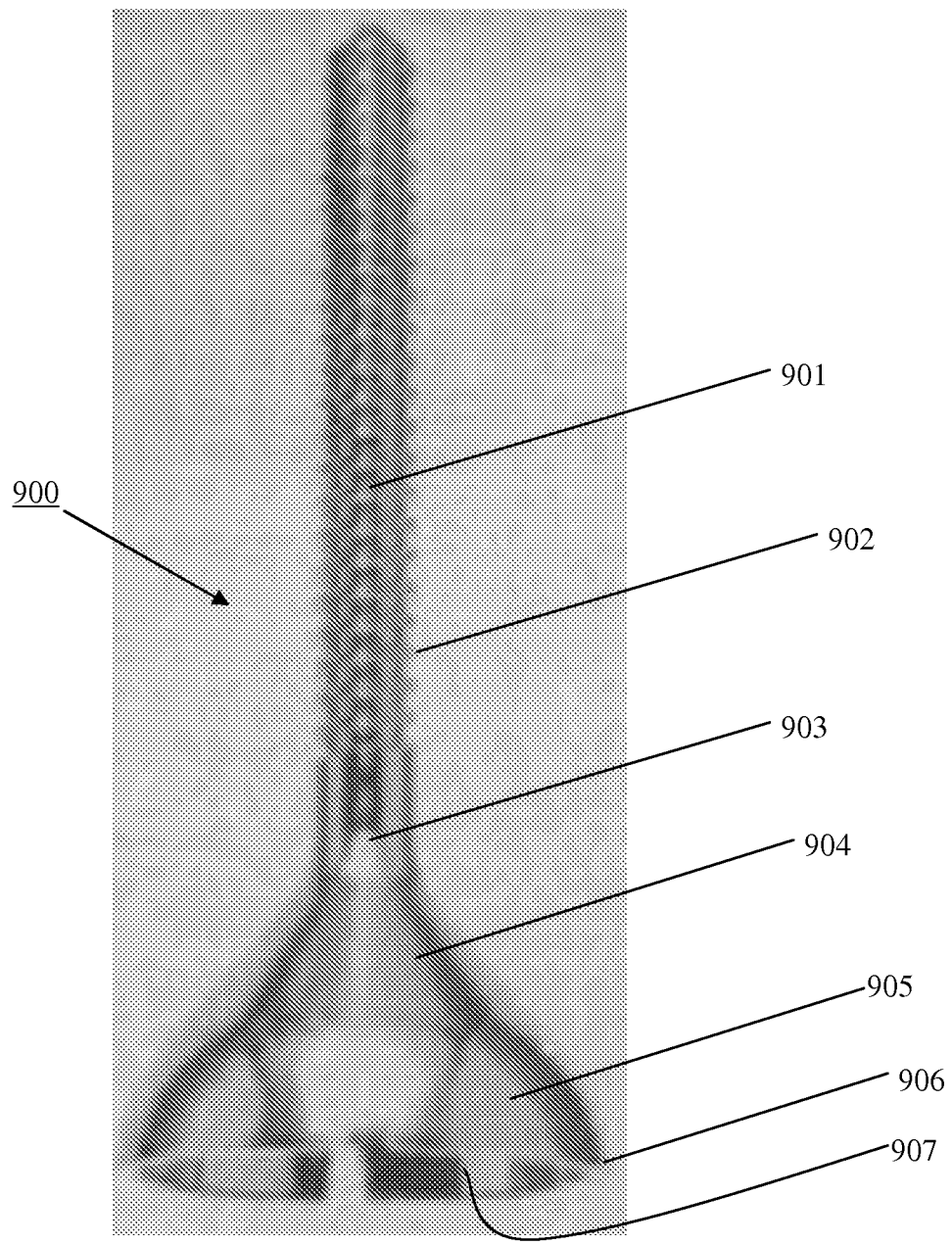
FIG. 1 is a front view of a prior art all-metal Ring prosthesis.
Figures 2A, 2B, 2C, 2D:
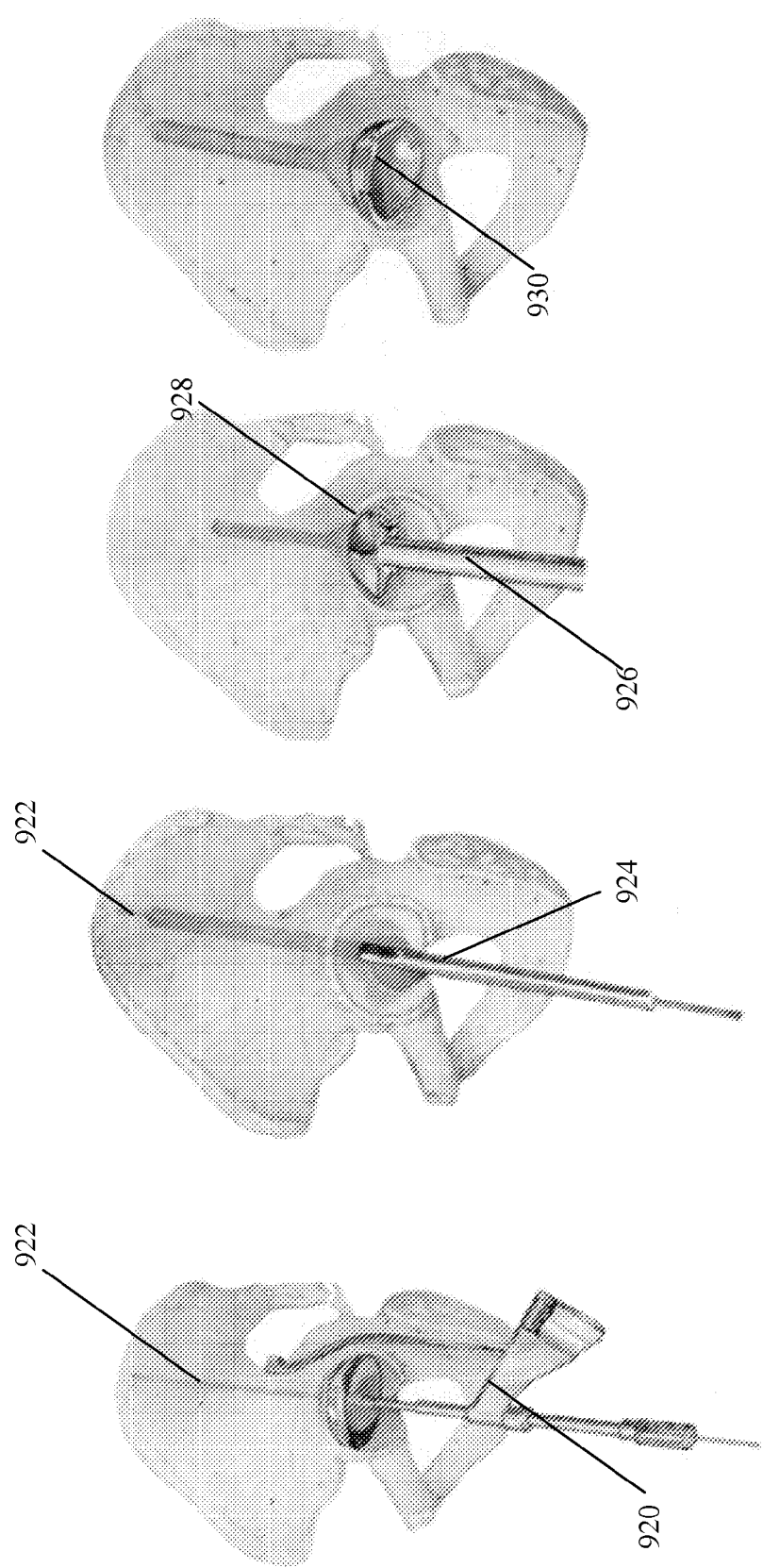
FIGS. 2a-d. illustrate the method of installing the prosthesis of FIG. 1.
Figures 3A, 3B:
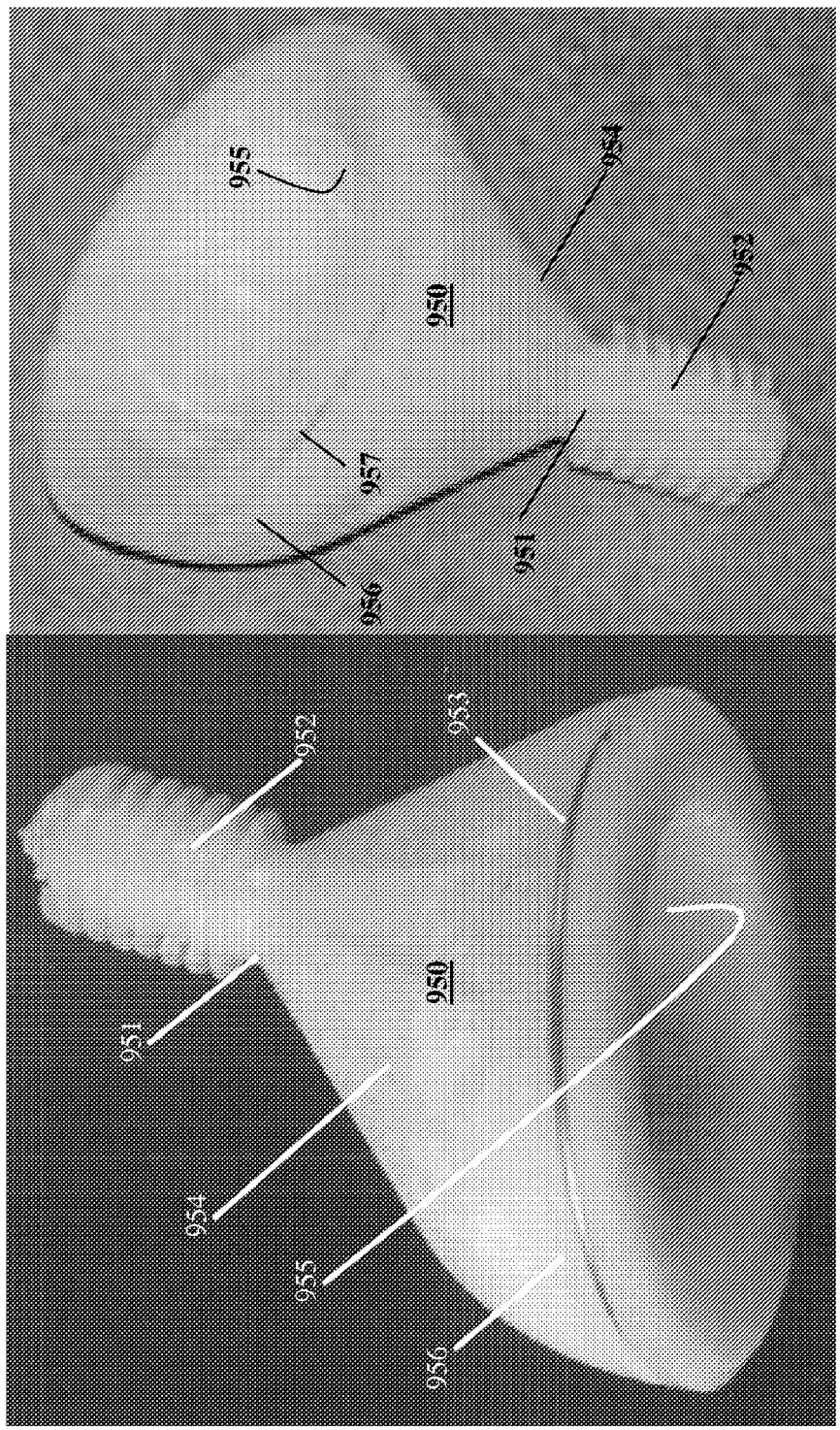
FIG. 3a-3b are frontal views of a prior art uncemented polyethylene-on-metal (UPM) hip prosthesis.
Figure 4:
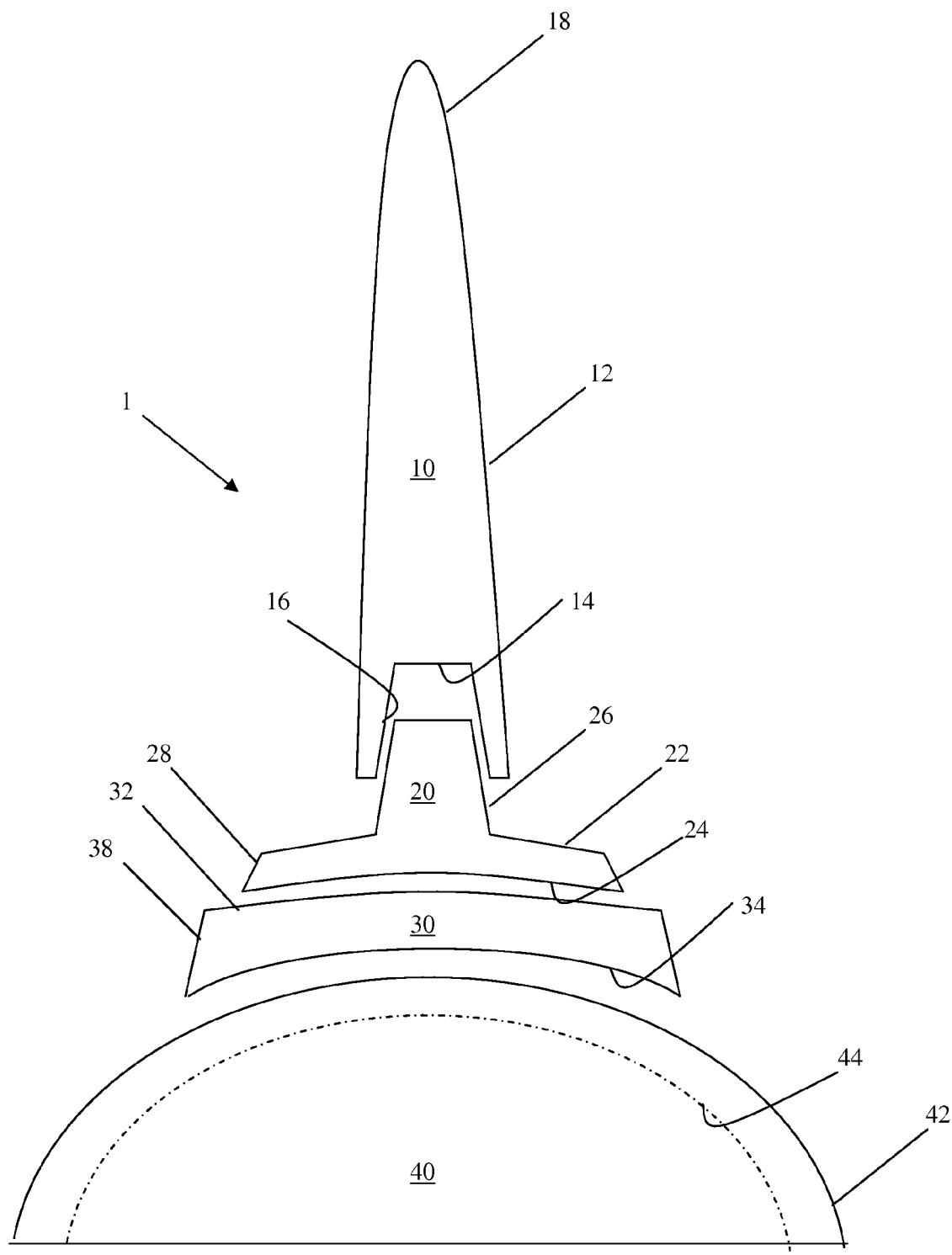
FIG. 4 is a front view of an acetabular prosthesis according to one embodiment of the present invention.

FIG. 4 illustrates an acetabular prosthesis (1) according to one embodiment of the present invention. Prosthesis (1) may comprise a stem portion (10), first augment portion (20), second augment portion (30), and shell portion (40). The stem portion (10) may have an outer shank portion (12), tip portion (18), male or female tapered stem portion (16), and a taper end (14) located at a converging end of said male or female tapered portion (16). The first augment portion (20) may comprise a corresponding male or female tapered augment portion (26) that corresponds with and interlocks with said male or female tapered stem portion (16). The first augment portion (20) comprises stem-side surface geometries (22), shell-side surface geometries (24), and peripheral geometries (28) which may be as simple or complex as is necessary to optimally fit a predetermined patient population or individual patient. An optional second augment portion (30) also having stem-side surface geometries (32), shell-side surface geometries (34), and peripheral geometries (38) may be used in combination with said second augment portion (20), in order to increase the offset of the shell (40), or to provide a gap space filler so as to reduce the amount of cement used between the shell (40) and stem (10) to secure the shell (40). Shell (40) comprises an outer (42) and inner (44) geometry. The inner geometry (44) may be a bearing surface for articulation with a natural or artificial femoral head component, or it may be configured to receive a liner that articulates with a natural or artificial femoral head component. The outer geometry (42) may be any geometry as simple or complex as is necessary to optimally fit a predetermined patient population or individual patient, but is preferably formed by a hemispherical porous structure.

FIGS. 5*a-f* illustrate several options for outer shank portions (12) within the scope of the present invention. FIG. 5*a* illustrates a smooth outer shank portion (12*a*) suitable for cementing into the ilium canal. FIG. 5*b* illustrates a fluted outer shank portion (12*b*), suitable for preventing rotation of the stem (10) within the iliac canal and to provide some amount of flexibility to the stem (10). FIG. 5*c* illustrates an outer shank portion (12*c*) of a stem (10), which comprises any one of hydroxyapatite, BMP, antimicrobial-infused hydroxyapatite, analgesic, or other coating thereon. FIG. 5*d*. illustrates a stem portion (10) having an outer shank portion (12*d*) comprised of a porous scaffold such as titanium foam, porous ceramic (e.g., hydroxyapatite), sintered beads, sintered asymmetric particles, or the like. FIG. 5*e*. illustrates an outer shank portion (12*e*) of a stem (10) comprising screw fixation means, such as a self-threading profile. FIG. 5*f*. illustrates a stem (10) fixed to the IM iliac canal with lag screws (12*f*).

FIG. 6*a-d* illustrate stem tips according to several different embodiments within the scope of this invention. The end of stem (10) may be bullet-shaped as shown in FIG. 6*a*, cone-shaped as shown in FIG. 6*b*, cylindrically-shaped as shown in FIG. 6*c*, or bi-forked as shown in FIG. 6*d* to reduce pain. The stems (10) may be stepped or chamfered in profile, and may include combinations of the features shown in FIGS. 5*a*-7.

FIG. 7 illustrates a modular stem composed of at least a first stem part (10') and a second stem part (10"). The first stem part (10') may be, for instance, a shaped porous augment. The second stem part (10") may be, for instance, a solid cap having a male taper (16") portion thereon, which is configured to mate with a first (20) or second (30) augment portion. If the first stem part (10') is formed of a low-strength porous construct, it may be cannulated to receive a core portion integral or separate from the second stem part (10") to increase the overall strength of the modular stem.

FIGS. 8*a-d* illustrate different first augment portion (20) configurations. Augment portions (20) may be configured with a male or female tapered augment portion (26*a*, 26*b*, 26*c*, 26*d*) that is designed to cooperate and interlock with a corresponding male or female tapered stem portion (16). The male or female tapered augment portion (26*a*) may be concentric as shown in FIG. 8*a*, or the male or female tapered augment portion (26*b*) may be eccentric as shown in FIG. 8*b*. Alternatively, the male or female tapered augment portion (26c) may be centrally-attached and oblique as shown in FIG. 8c, or the male or female tapered augment portion (26d) may be eccentric and oblique as shown in FIG. 8d. By changing the configurations of the male or female tapered augment portions (26a, 26b, 26c, 26d), intraoperative adjustability is increased.

As shown in FIGS. 8a-d, augments (20) of the present invention may comprise offsets and different shell-side geometries (24, 27). Shell-side geometries may be more curved (27, 27', 27") or less curved (24, 24', 24"). Augment portions (20) may further comprise different shell-side geometry offsets. For example, a shell-side geometry may comprise a standard offset (24), a medium offset (24'), and/or a high offset (24").

FIGS. 9a-f illustrate augment configurations according to some embodiments of the present invention. Augment (20) may be provided as a single, homogeneous metallic, ceramic, or polymeric piece having a smooth surface (29a) as shown in FIG. 9a, or the augment (20) may comprise two pieces press-fitted together. A coating (29b) or the like, such as hydroxyapatite, bone cement, or bone-void filler may be applied to the outside of augment (20) in one or more regions around the male or female tapered augment portions (26a, 26b, 26c, 26d) as shown in FIG. 9b. Alternatively, a porous structure (29c) may be formed as a portion of said augment (20). Holes (25a-i) may be formed within augments (20) of the present invention in order to secure said augments (20) to surrounding bone and lock the radial orientation of the augment (20) with respect to the orientation of the stem portion (10).

FIGS. 9g-i illustrate augments in combination with wedges and spacers according to some embodiments of the present invention. A series of wedges (100) or offset spacers (102) may be utilized to "build up" the acetabular region where larger bone portions have been compromised. Shaped or special wedges (104) may be utilized for direct mounting to an acetabular shell. Hemispherical offset spacers (106, 108) may also be utilized to adjustably mount an acetabular shell (40) to the stem portion (10). One or more spikes (25j) may be optionally employed on the wedges (100, 104), augments (20, 30), and spacers (102, 106, 108) in order to help bony fixation, prevent rotation, and help create stability between said augments, spacers, and wedges.

FIG. 10 shows a cemented acetabular prosthesis (1) according to some embodiments of the present invention. The prosthesis (1) comprises a stem portion (10), a first augment portion (20), a second augment portion (30) and a shell portion (40). The first augment portion (20) is configured to form a taper-lock connection with the stem portion (10). An optional first means for fixation (50), such as a screw having a countersunk head (53) and threaded shaft (51) may be inserted through a bore (21) in the first augment portion (20) and into a threaded bore (11) in the stem portion (10). The bore (21) may have a countersink (23) adapted to receive a portion (53) of said optional first means for fixation (50). Optionally, a second means for fixation, such as a fastening screw (60) may be inserted through a hole (25) in the first augment portion (20) in order to secure the first augment portion (20) to surrounding bone and prevent rotation of the first augment portion (20) relative to the stem portion (10).

A second augment portion (30) may be utilized to space an acetabular shell (40) further from the stem (10). Second augment portion (30) preferably has an appropriately sized and shaped peripheral profile (38) so as to allow its stem-side face (32) to contact the first augment portion (20).

FIG. 11 shows a cemented acetabular prosthesis similar to the one shown in FIG. 10; however, the second augment portion (30) does not utilize optional second means for fixation (60) to secure the second augment portion (30) against the first augment portion (20). Instead, first means for fixation (50) protrudes through one of at least one tapered bore (33) in the second augment portion (30). Said first means for fixation (50) protrudes through a clearance bore (21) in the first augment portion (20) and into a threaded bore (11) in the stem portion (10). The countersunk head (53) of the first means for fixation (50) rests within the one of at least one tapered bore (33) below the shell-side surface (34) of the second augment portion (30). Different prosthesis configurations may be achieved by utilizing the means for fixation (50) with a different bore (33).

FIG. 12 shows a cemented acetabular prosthesis according to other embodiments of the present invention. The prosthesis (1) shown in FIG. 12 is similar to those shown in FIGS. 10 and 11, with the exception that a second augment portion (30) is not utilized. Instead, the shell-side surface (24) of the first augment portion (20) serves as a cement dam for a cement reservoir (70) between the first augment portion (20) and shell portion (40). Since the first augment portion is rigidly secured to the stem portion (10), and the shell (40) is cemented to the first augment portion (20), all portions (10, 20, 40) are rigidly fixed to each other. Cement reservoir (70) provides a means for independently adjusting the position and orientation of the shell portion (40), while still utilizing the stable platform of the first augment portion (20) and stable foundation of the stem portion (10).

Figure 13:
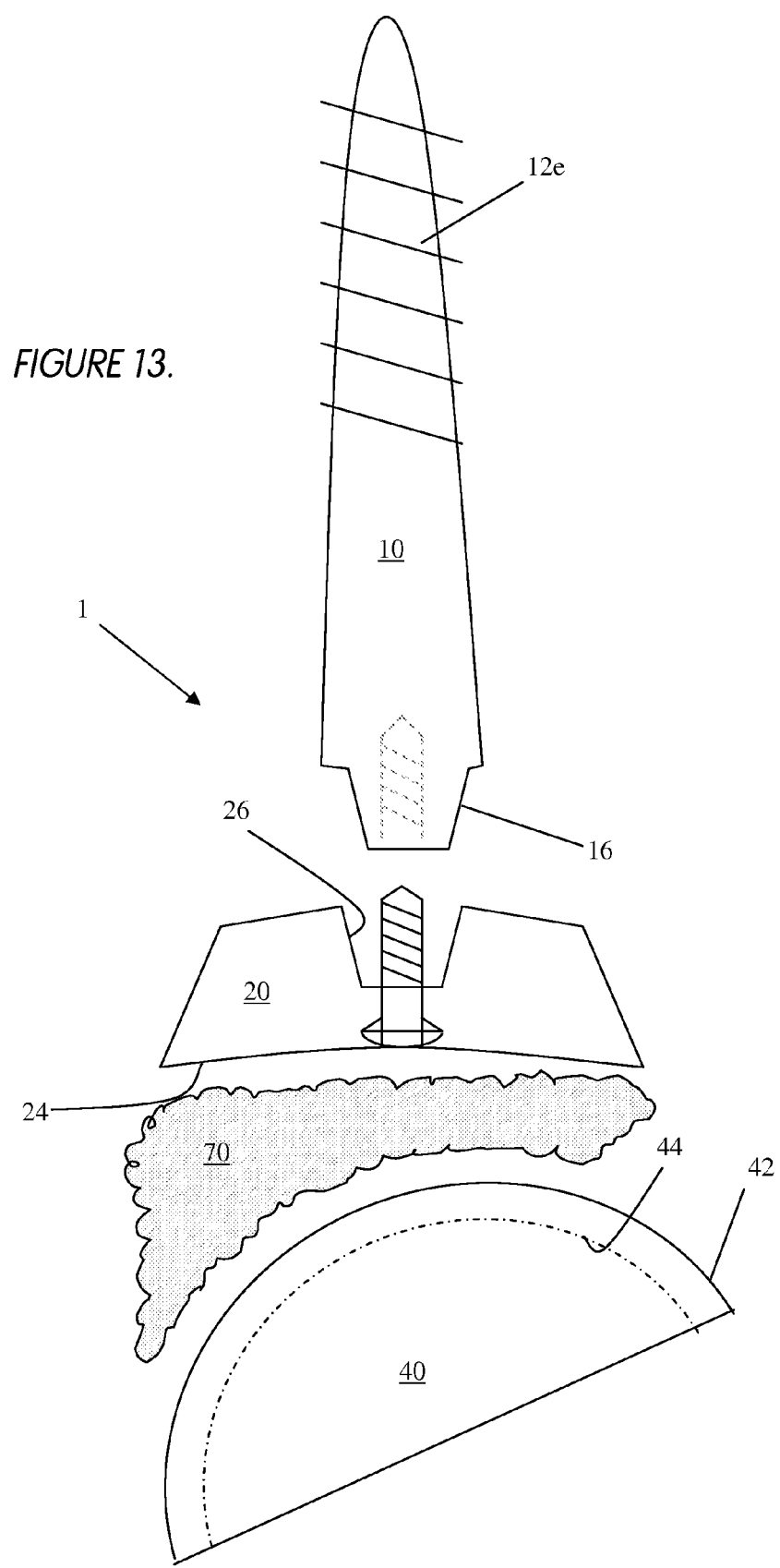
FIG. 13 shows a cemented acetabular prosthesis according to yet other embodiments of the present invention.

FIG. 13 shows a cemented acetabular prosthesis according to yet other embodiments of the present invention. Stem portion (10) has a threaded outer profile (12e) which serves as means for fixing said stem portion (10) to a prepared or non-prepared iliac canal. Stem portion includes a male or female tapered portion (16) which mates and taper-locks with a male or female tapered portion (26) on a first augment portion (20). First augment portion has a shell-side surface (24) which serves as a cement dam for a cement reservoir (70) bonding an acetabular shell portion (40) to the first augment portion (20). Each of the stem portion (10), first augment portion (20), and shell portion (40) are fixedly secured together and anchored directly or indirectly to the iliac canal for improved stability. Prior to curing, cement reservoir (70) provides a means of adjustably mounting the shell portion (40) to the rest of the prosthesis (1) and surrounding bone.

Figure 14:
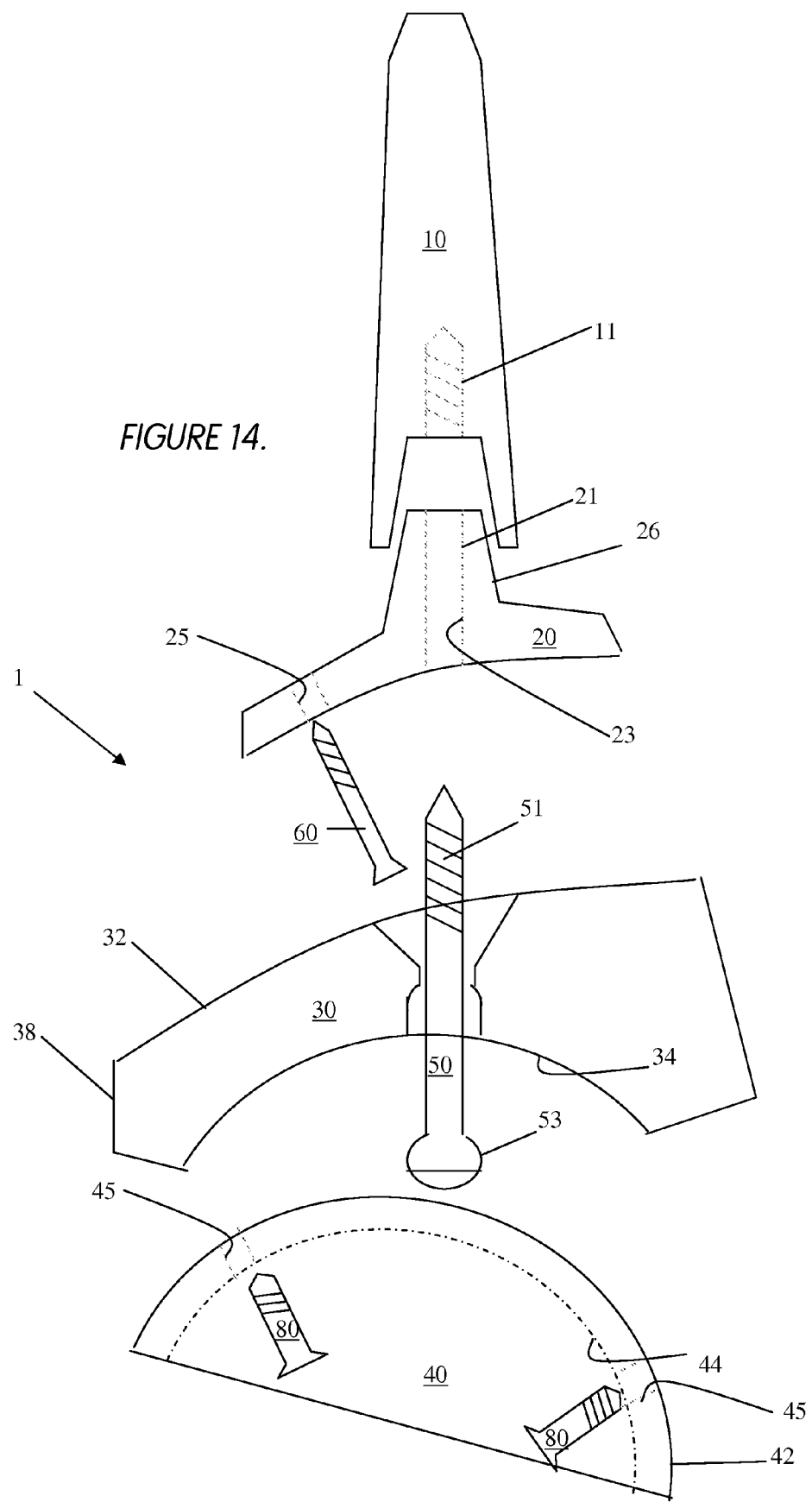
FIG. 14 shows a cementless acetabular prosthesis according to some embodiments of the present invention.

FIG. 14 shows a cementless acetabular prosthesis according to some embodiments of the present invention. The prosthesis (1) is very similar to the one shown in FIG. 11. However, the second augment portion (30) is formed from a polymeric material such as PEEK, UHMWPE, polyethylene, polyurethane, or the like, and, the first augment portion (20) comprises an eccentric and oblique tapered portion (26). A means for fixation (50) comprising a means for adjustment (53) is provided to secure each of the stem portion (10), first augment portion (20), and second augment portion (30) together, while providing infinite rotational adjustability between the stem portion (10) and the first augment portion (20), and infinite tangential motion and infinite rotation adjustability between the first (20) and second (30) augment portions within a predetermined range. The acetabular shell portion (40) has mounting holes (45) and means (80) for securing the acetabular shell portion (40) to the second augment portion (30). Said means (80) for securing may comprise self-threading, self-tapping screws which are designed to self-thread directly into the polymeric second augment portion (30). In one preferred embodiment, first (20) and second (30) augment portions are combined into a single pre-assembled augment piece by connecting means. Connecting means may be detachable and comprise an adjustable linkage, a snap mechanism, or a mechanical interlocking device. Alternatively, the connecting means may be non-detachable and comprise mechanical fusing, chemical bonding, fusion molding, or adhesives. While any material may be chosen, it is preferred that first augment portion (20) be made of a metallic material, and second augment portion (30) be made of a polymer.

Figure 15:
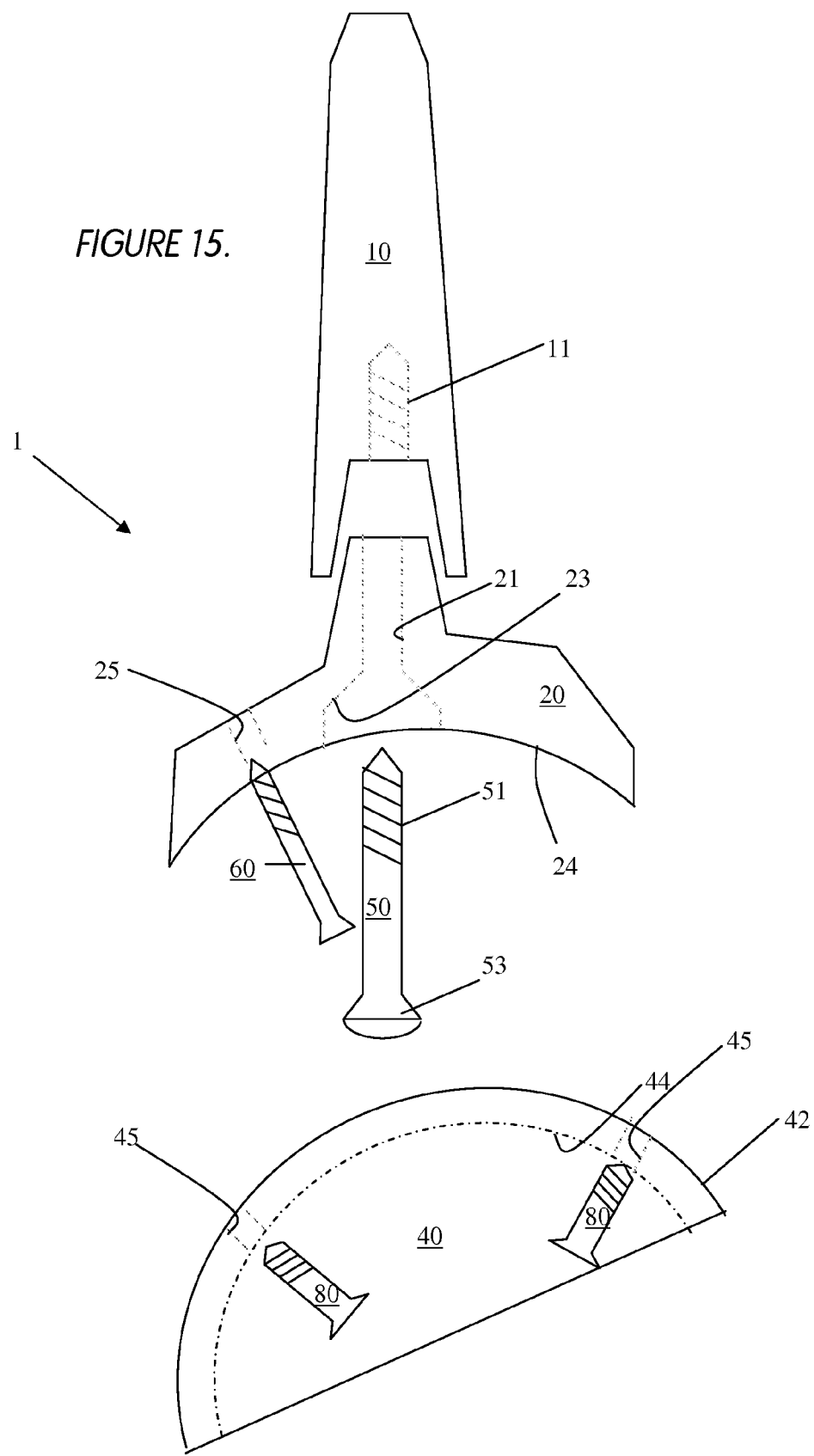
FIG. 15 shows a cementless acetabular prosthesis according to other embodiments of the present invention.

FIG. 15 shows a cementless acetabular prosthesis according to other embodiments of the present invention. The second augment portion (20) is shaped so as to have a shell-facing surface (24) that conforms to the outer surface (42) of an acetabular shell portion (40). Means (80) for securing the acetabular shell portion (40) to the first augment portion (20) is provided. Said means (80) may be, for instance, a screw or peg which is adapted to pass through holes (45) in the shell portion (40) and thread directly into the material of the first augment portion (20). First augment portion (20) may comprise a polymeric material, metallic material, or ceramic material, and may or may not comprise porous portions. Materials for first augment portion (20) may include, but are not limited to porous hydroxyapatite (HA), porous titanium, and porous tantalum. Optional first means for fixation (50) may include a countersunk head (53) which rests below said shell-facing surface (24).

Figure 16:
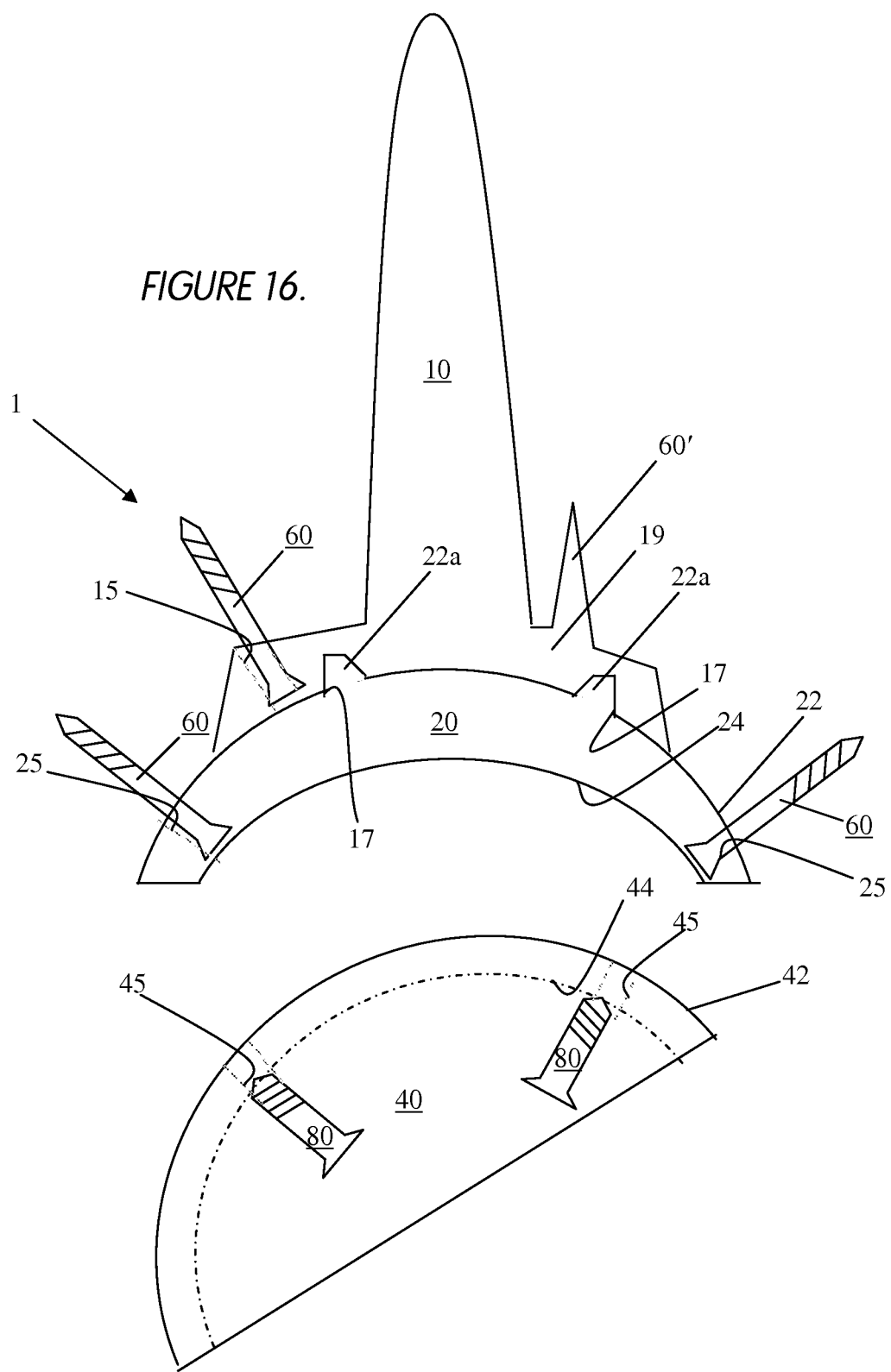
FIG. 16 shows a cementless acetabular prosthesis according to yet other embodiments of the present invention.

FIG. 16 shows a cementless acetabular prosthesis according to yet other embodiments of the present invention. The stem portion (10) comprises an integral flange portion (19) and one or more optional second means for fixation (60) such as one or more cortical or cancellous bone screws or one or more integral spikes (60'). A first augment portion (20) comprises a generally hemispheric augment having one or more orientation or fixation protuberances (22a). Protuberances (22a) are configured to fit into one or more complimentary recesses (17) located on portions of the stem portion (10), for instance, adjacent the flange portion (19). If there are more recesses (17) than there are protuberances (22a), then the first augment portion (20) can be situated, positioned, oriented, and fixed in many ways relative to the stem portion (10). Optional second fixation means (60) may be used to secure the first augment portion (20) to surrounding bone, and also to press stem-side surface (22) of the first augment (20) against the shell-side surface of the stem portion (10) and/or flange portion (19). The shell-side surface (24) of the first augment portion (20) may be configured to conform to the external geometries (42) of an acetabular shell portion (40). Means (80) for securing said shell portion (40) may be used to secure the shell portion (40) to the first augment portion (20) or to surrounding bone. For instance, and without limitation, if the first augment portion is made of porous metal, holes (not shown) aligned with mounting holes (45) found in the shell portion (40) would be drilled into the first augment portion (30), and then means (80) would be screwed into said holes (not shown). Alternatively, if the first augment portion (20) is made of a polymeric material (e.g., PEEK), and means (80) comprises self-tapping, self-threading screws, then said means (80) could be screwed directly into the material of the first augment portion (20) to secure the shell portion (40) to the first augment portion (30), without drilling.

Figure 17:
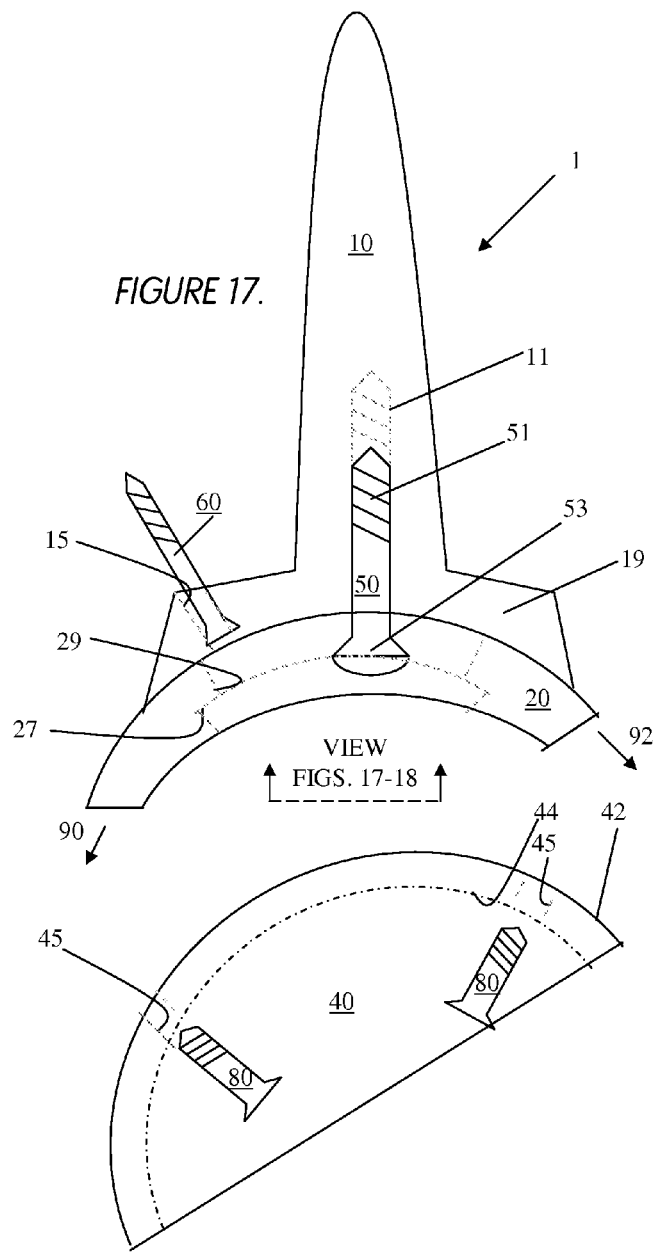
FIGS. 17-19 show a cementless acetabular prosthesis according to embodiments of the present invention which utilize a track system for adjustable mounting.
Figure 18:
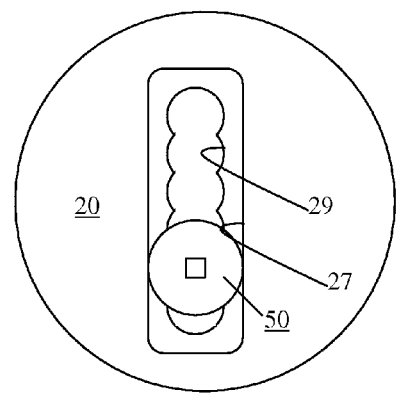
Figure 19:
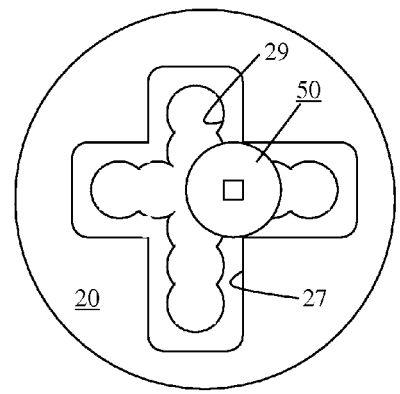

FIGS. 17-19 show a cementless acetabular prosthesis (1) according to embodiments of the present invention which utilize a positioning portion which may include an adjustable track (27, 29) in combination with a means (50) for fixing a first augment portion (20) to a stem portion (10). Positioning portion (27, 29) includes a countersink (27) large enough for a head portion (53) of said means (50) for fixing. Track (27, 29) further includes a slot composed of a series of cutouts (29) for a threaded shank (51) of said means (50) to pass. The means for fixing (50), may, for instance, comprise a screw that can be loosened from a threaded bore (11) in a stem portion (10). When said screw (50) is loosened, the first augment portion (20) can be moved in different directions (90, 92) corresponding to the geometries of said track (27, 29). When a desired position of the first augment portion (20) relative to the stem portion (10) is determined, the screw (50) is tightened such that its head (53) rests within one of said cutouts (29). Friction holds the first augment portion (20) to the stem portion (10). Thereafter, an acetabular shell portion (40) can be attached to the first augment portion (20) by means (80) described in any of the above embodiments.

Figure 20:
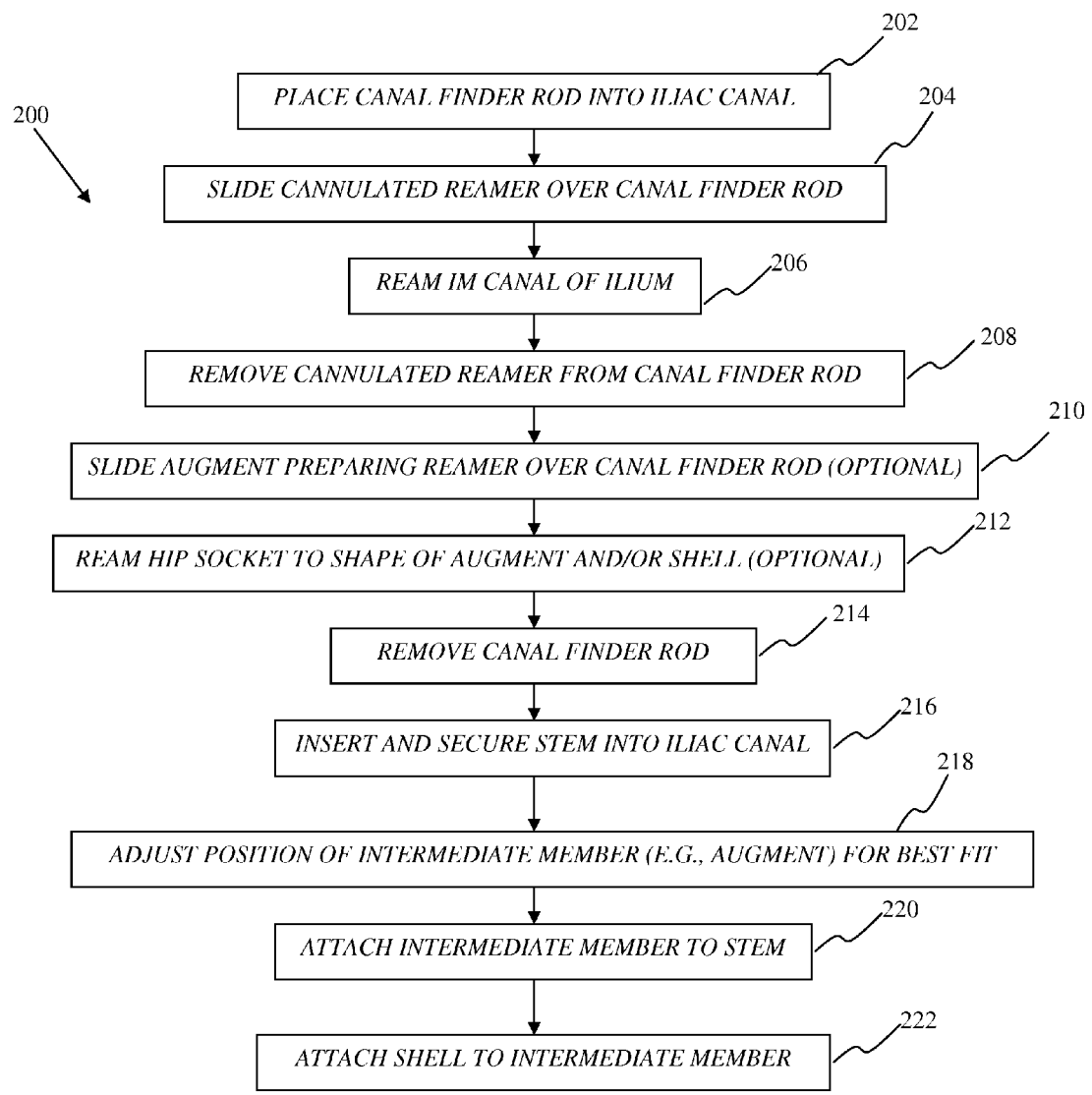
FIG. 20 is a schematic flowchart illustrating some surgical technique method steps of installing an acetabular prosthesis according to the present invention.

FIG. 20 is a schematic flowchart illustrating some surgical technique method steps (200) for installing an acetabular prosthesis according to some embodiments of the present invention. First, the canal of the ilium is found using a canal guide tool or the like (202). Second, the iliac canal is reamed (206) to accept the size of the stem portion (10) used. The reaming step may utilize a cannulated reamer that slides over the canal guide (204). All instrumentation (that is, the canal guide and/or reamers associated therewith) is then removed from the prepared iliac canal (208, 214). Secondary reaming or resection may take place (210, 212) depending on the shapes and configurations of the augments and present bone defects. A stem portion (10) is then inserted into and secured to the iliac canal (216) in any convenient fashion so as to form a "foundation" on which reconstruction of the acetabulum with augments, spacers, and wedges can be performed. One or more augments and/or other intermediate members is then placed in the acetabular region (218) in a predetermined position so as to form a platform that rests upon said stem portion (10)—thereby providing a base foundation for other augments, spacers, wedges, and/or cement reservoirs (70) to rest upon and secure to (220). Other acetabular preparation steps such as reaming for shell press fit and autograft packing may also be implemented. Lastly, a shell member (40) is attached to the one or more augments and/or intermediate members (222). The augments and/or intermediate members serve as means for adjustably securing a bearing surface to an acetabulum using a stem (10) situated within the iliac canal (504), the stem (10) serving as a support and/or orientation member.

Figures 21, 22:
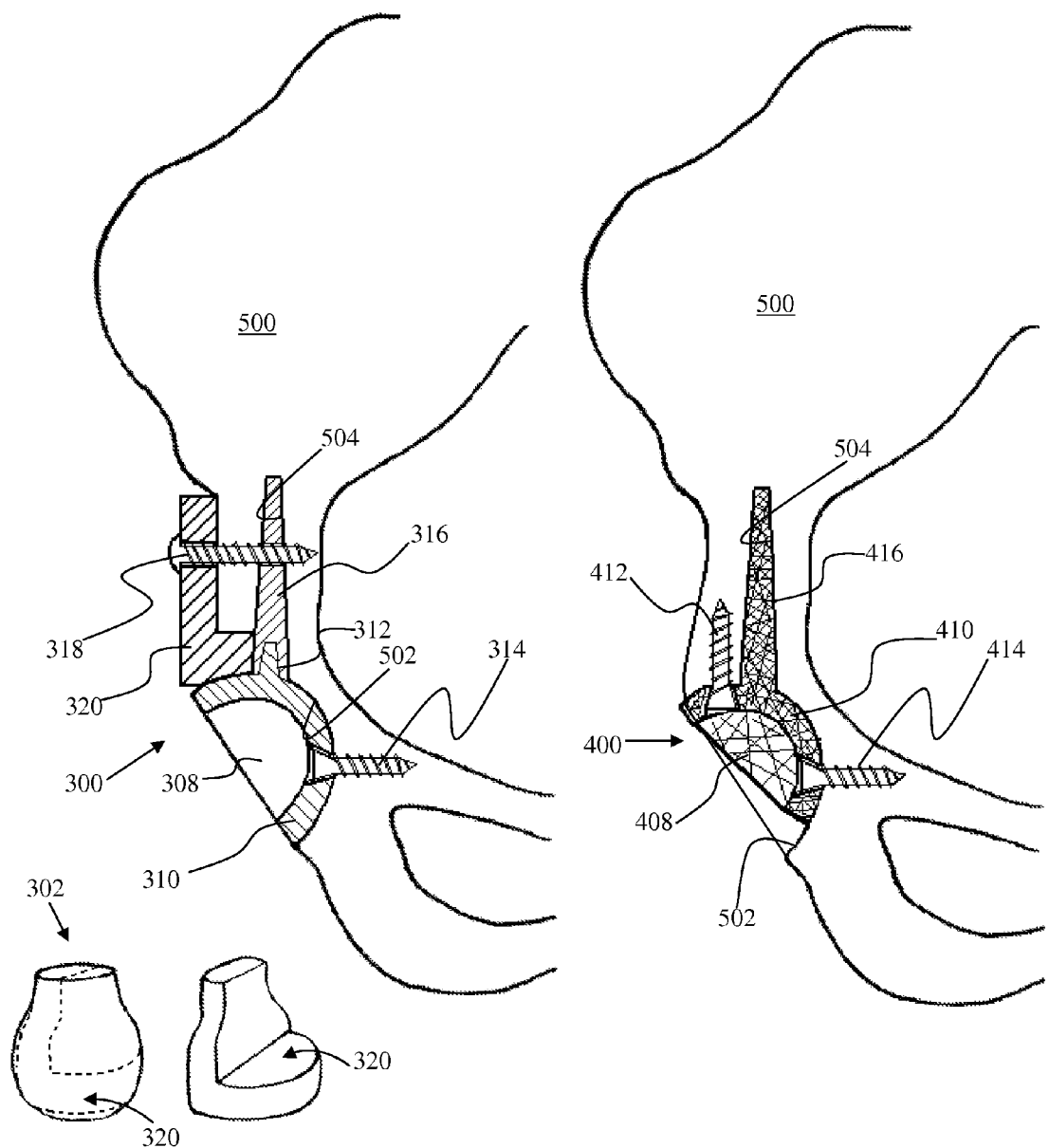
FIG. 21 shows a cementless acetabular prosthesis connected to an L-shaped allograft by a transverse screw which may be targetally-fixed to a stem portion of said prosthesis.
FIG. 22 shows a homogenous, monolithic porous augment having a protrusion adapted for insertion and securement to the intramedullary canal of the ilium.

FIG. 21 shows a cementless acetabular prosthesis (300) connected to allograft (320) by a transverse screw (318) fixed to a stem portion (316) of said prosthesis (300). The allograft (320) may be L-shaped and can be provided as a medical product, or it may be provided intraoperatively by shaping portions of a resected femoral head (302). Prosthesis (300) comprises a shell augment portion (310) having an outer surface adapted for resting against an acetabular cavity (502) within the ilium (500). An inner surface (308) of the augment portion (310) is adapted for a cement mantle interface or uncemented frictional interference with a secondary shell or liner. Alternatively, the inner surface (308) is provided with a bearing surface to make contact with a natural or prosthetic femoral head (not shown). Inner surface (308) may be adapted for securement of one or more additional porous or solid augments thereto via any one or more of a roughened surface for frictional contact, mechanical interlocking means, or cement. Secondary fixation means (314) may be utilized to improve stability of the prosthesis (300). Preferably, an intramedullary canal (504) of the ilium (500) is prepared and then a stem portion (316) is inserted therein. The augment portion (310) is situated in the acetabular cavity (502) and then locked to the stem portion (316) via a connection portion (312). Connection portion (312) may comprise a Morse taper lock or any other known locking means such as a threaded connection, screw, retainer ring, ball detent, or resilient snap fingers. Stem portion (316) may be provided with means for attaching the L-shaped allograft (320) such as a threaded bore or aperture for k-wire insertion.

FIG. 22 shows a cementless acetabular prosthesis (400) comprising a homogenous, monolithic porous augment (410) having a protrusion (416) adapted for insertion and securement within the intramedullary canal (504) of the ilium (500). Protrusion (416) may have different shapes and lengths depending on the severity of the defect or the size of the intramedullary canal (504). The augment (410) may be formed from any one of a reticulated foam structure, sintered beads, and sintered asymmetric particles without limitation, and may comprise titanium, tantalum, zirconium, bioceramics (porous hydroxyapatite), polymers (e.g., PEEK, UHM-WPE), biocompatible materials, and compositions thereof.

The intramedullary canal (504) of the ilium (500) is preferably prepared prior to insertion of the augment (410); however, this step may not be necessary. In addition to the protrusion (416), one or more secondary fixation means (412, 414) may be used to secure the augment (410) to the acetabular bone (502). The inner surface portions (408) of the augment (410) are adapted for a cement mantle interface or uncemented frictional interference with a secondary shell or liner. Alternatively, the inner surface (308) may be provided with a separate bearing surface to make contact with a natural or prosthetic femoral head (not shown). Inner surface (308) may also be adapted for securement of one or more additional porous or solid augments thereto via any one or more of a roughened surface for frictional contact, mechanical interlocking means, or cement.

Figure 23:
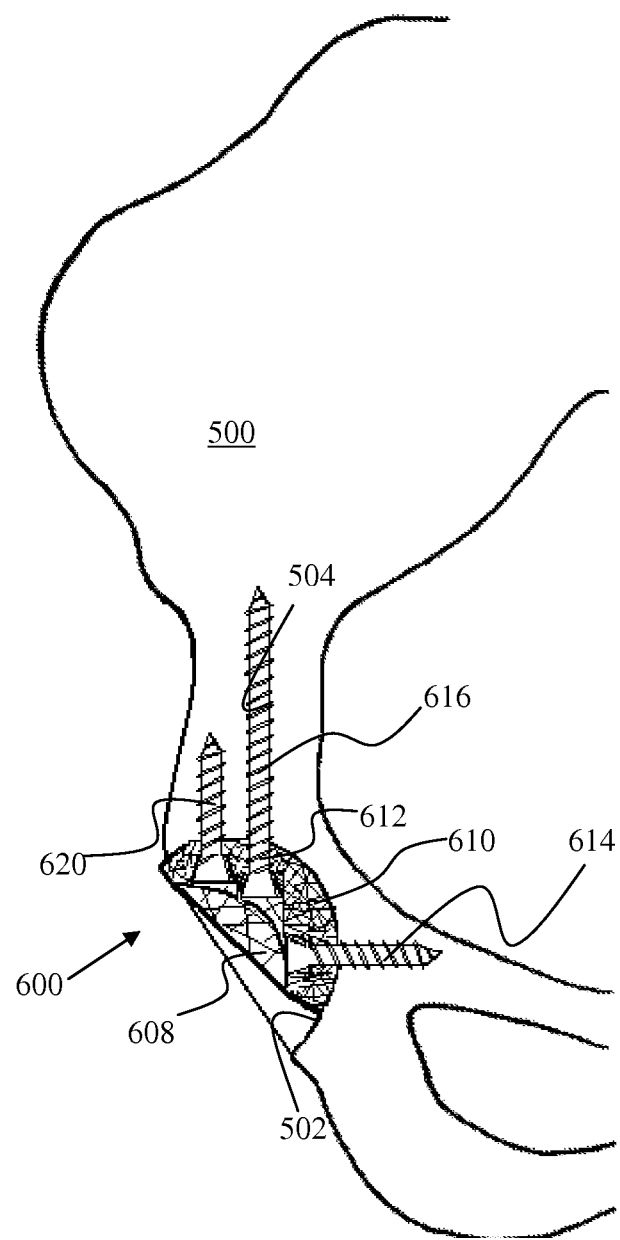
FIG. 23 shows an augment according to the present invention which is provided with a means for peg or screw-mounting into the intramedullary canal of the ilium.

FIG. 23 illustrates an uncemented prosthesis (600) according to some embodiments of the present invention. The prosthesis (600) comprises a porous augment (610) adapted to fill a bone void in an acetabular region (502). The augment (610) comprises inner surface portions (608) which are adapted for a cement interface or uncemented frictional interference with a secondary shell or liner. Alternatively, the inner surface portions (608) may be provided with a separate bearing surface to make contact with a natural or prosthetic femoral head (not shown). Inner surface portions (608) may also be adapted for securement of one or more additional porous or solid augments thereto via any one or more of a roughened surface for frictional contact, mechanical interlocking means, or cement.

The porous augment (610) comprises a means for mounting itself to an intramedullary canal (504) of the ilium (500). The means for mounting may comprise, for instance, an aperture or channel (612) having a countersink and which is properly oriented such that when the augment (610) is fully seated in the acetabular cavity (502), a peg or screw (616) may be inserted through the augment (610) and into the intramedullary canal (504) of the ilium (500) to fixedly secure the augment (610) to the acetabulum (502). Secondary fixation means (614, 620) may be used for additional augment stability. Once the uncemented prosthesis (600) is implanted, an acetabular cup prosthesis (not shown) can be mounted to the inner surface portions (608) using friction, cement, or screws.

Figure 24:
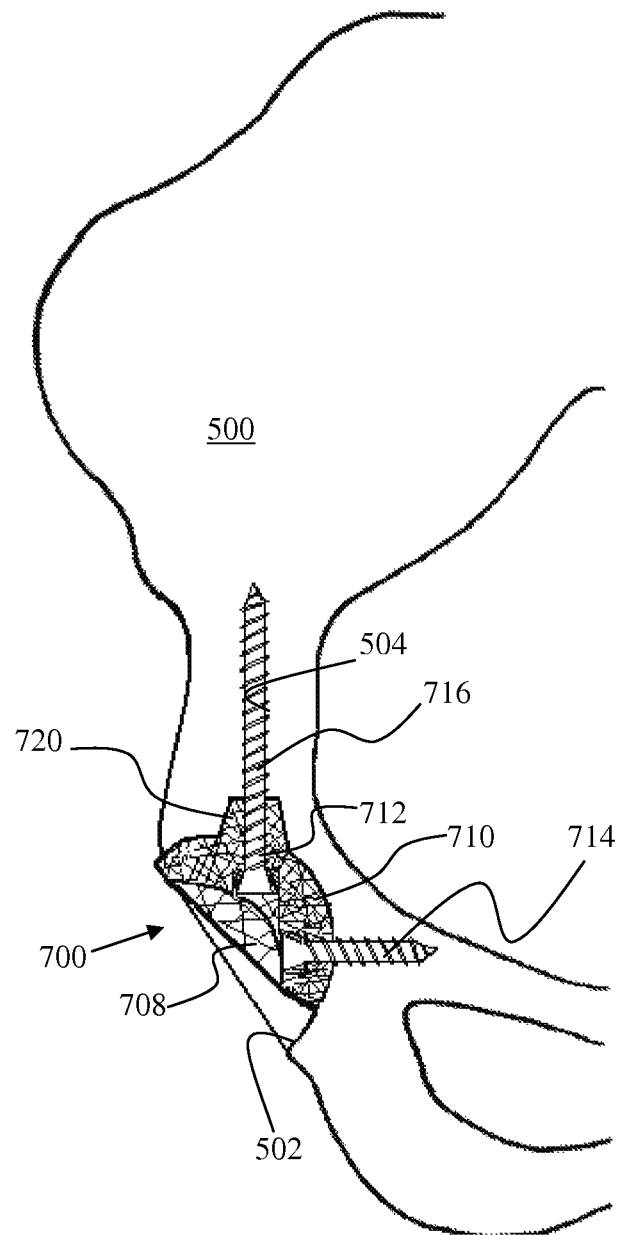
FIG. 24 shows an augment similar to the one shown in FIG. 23, but having a protrusion for filling a void surrounding the entrance of the intramedullary canal of the ilium.

In some embodiments, such as the one illustrated in FIG. 24, a cementless prosthesis (700) may comprise a porous augment (710) having an inner surface (708) and outer surface configured for frictional engagement with acetabular bone (502). The augment (710) may comprise a protrusion (720) that extends around an entrance portion of the intramedullary canal (504) of the ilium (500). The protrusion (720) may include one or more means (712) for securing a fixing device (716) thereto. The fixing device (716) may be a screw, a peg, a rod, or a detachable stem portion without limitation. The fixing device (716) is inserted into the intramedullary canal (504) of the ilium (500) to orient and secure the augment (710) within the acetabulum (502). Secondary means for fixation (714) may be employed to achieve greater stability. It should be noted that inner surface portions (708) may be adapted for securement of one or more additional porous or solid augments thereto via any one or more of a roughened surface for frictional contact, mechanical interlocking means, or cement. Alternatively, inner surface portion (708) may be provided with a bearing surface for articulation with a natural femoral head or a femoral head implant component (not shown).

Figure 25:
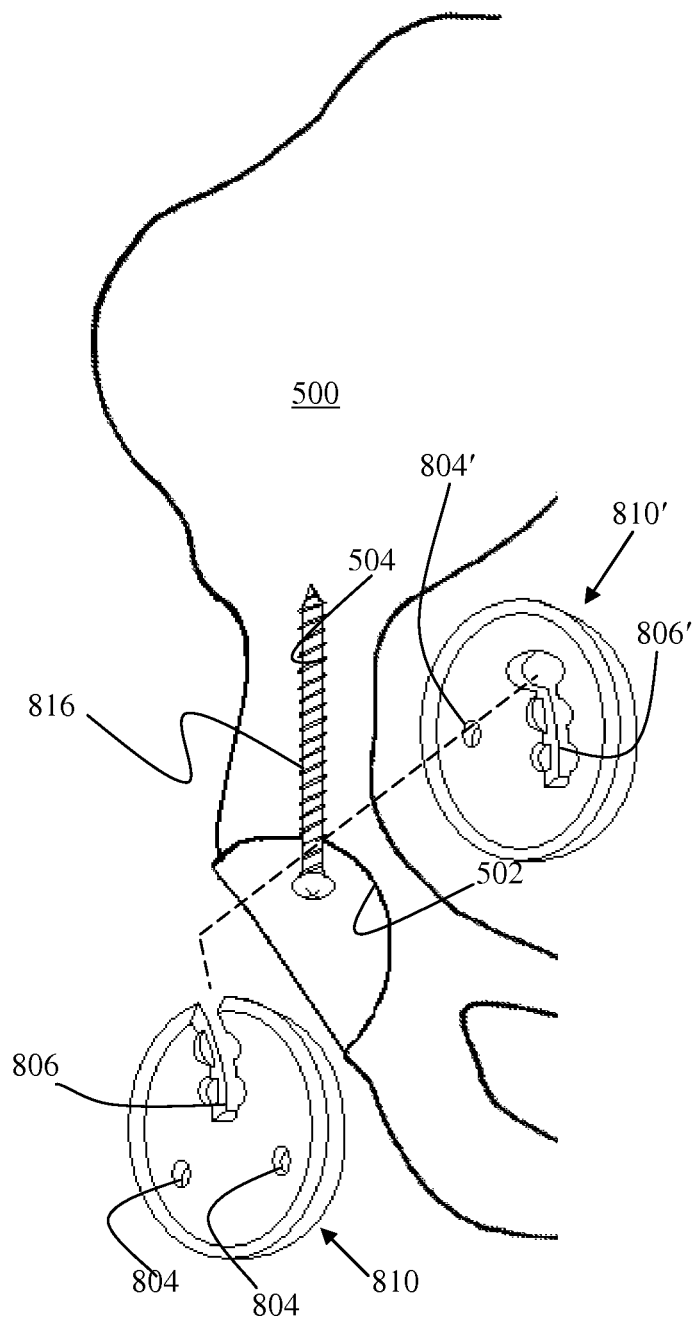
FIG. 25 shows an augment similar to the one shown in FIG. 23, which is capable of being mounted to an acetabulum after a fixation device such as a peg or screw is inserted into an intramedulary canal of the ilium.
Figure 26:
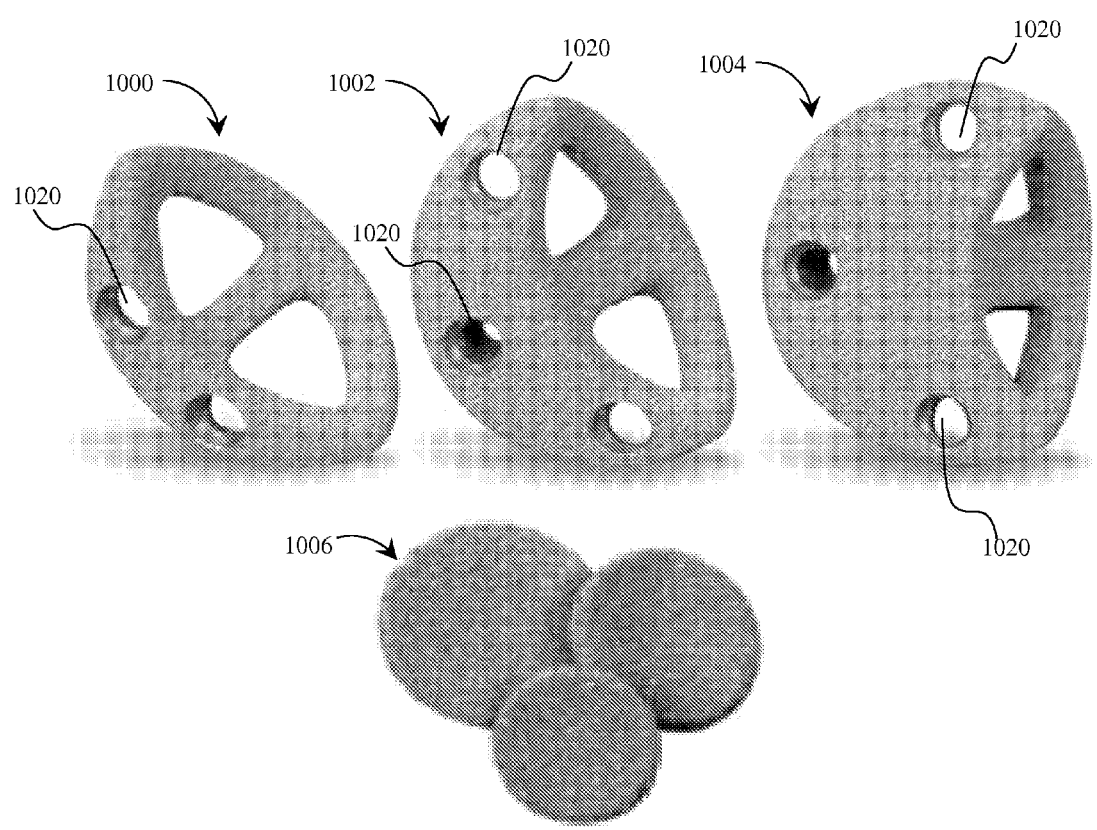
FIG. 26 shows some examples of prior art acetabular augments provided by Zimmer, Inc., which do not have protrusion portions configured for insertion into the IM canal of the ilium, and, which do not have a means for inserting a screw or means for mounting to the IM canal of the ilium.

In some embodiments, such as the one illustrated in FIG. 25, it may be desirable to secure a means for fixation (816) such as a rod, peg, or screw, to the intramedullary canal (504) prior to attaching the augment (810, 810'). In such cases, the means for fixation (816) may be partially inserted into the intramedullary canal (504) of the ilium (500) to allow room for the augment (810, 810') to be introduced from a medial, lateral, anterior, posterior, or inferior side. Once the augment (810, 810') is properly positioned, the means for fixation (816) may then be fully inserted into the intramedullary canal (504) to tighten the augment (810, 810') to the acetabular cavity (502). In the embodiment shown, the augment (810, 810') is maintained against the acetabulum (502) via a countersink or shelf in a hole or slot (806, 806'). Secondary fixation means (804, 804') may be provided on the augment (810, 810') to better secure the augment (810, 810') to the acetabular cavity (502). For example, the secondary fixation means (804, 804') may be a hole or slot configured to accept a peg or bone screw.

It should be noted that any portions of the implants and prostheses disclosed herein may be formed as trial components and instrumentation for trial reduction. In some cases, the augments may be configured to snap together using mechanical interlocking means.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The following is claimed:

1. An acetabular prosthetic device for implantation in an iliac canal and acetabulum of an ilium, comprising:
a stem configured to be implanted in the iliac canal; and
an acetabular component comprising an acetabular outer shell configured to be implanted in the acetabulum and fixed to the stem, the acetabular outer shell including an external outer bone bearing surface, and further comprising a connection portion to adjustably connect the acetabular outer shell to the stem such that the acetabular outer shell is configured to be oriented in a plurality of orientations before being fixed to the stem, wherein the connection portion comprises at least one augment having a first curved surface geometry that substantially conforms to and is matingly engaged with a second curved surface geometry defined by the external outer bone bearing surface of the acetabular outer shell to selectively orient and position the acetabular outer shell relative to the stem, wherein the stem is rigidly engaged in abutment against an external surface of the at least on augment opposite the first curved surface geometry, wherein the first curved surface geometry of the at least on augment is rigidly engaged in abutment against the external outer bone bearing surface of the acetabular outer shell to fix the acetabular outer shell at a select orientation and position relative to the stem, and wherein the external outer bone bearing surface of the acetabular outer shell comprises a porous surface configured to promote bone ingrowth into acetabular outer shell.

2. The acetabular prosthetic device of claim 1, wherein the at least on augment is rigidly engaged with the stem by a taper lock to orient the augment with respect to the stem.

3. The acetabular prosthetic device of claim 2, wherein the at least one augment comprises a plurality of augments, each of the plurality of augments having a first surface configured to orient the augment with respect to the stem and a second surface of the augment configured to orient the acetabular outer shell with respect to the stem such that each of the plurality of augments orients the acetabular outer shell in a different orientation from at least one other of the plurality of augments.

4. The acetabular prosthetic device of claim 1, wherein the first curved surface geometry of the at least one augment is a concave surface and the second curved surface geometry defined by the external outer bone bearing surface of the acetabular outer shell is a convex surface, and wherein the concave surface of the at least one augment is fixedly engaged with the convex surface of the acetabular outer shell by bone cement.

5. The acetabular prosthetic device of claim 1, wherein the first curved surface geometry of the at least one augment is selectively engaged with the second curved surface geometry defined by the external outer bone bearing surface of the acetabular outer shell in an infinite number of circumferential positions along the external outer bone bearing surface of the acetabular outer shell.

6. The acetabular prosthetic device for implantation in an iliac canal and acetabular of an ilium, comprising:
    a stem configured to be implanted in the iliac canal; and
    an acetabular component configured to be implanted in the acetabular and fixed to the stem, the acetabular component further comprises a connection portion to adjustly connect the acetabular component to the stem such that the acteabular component is configured to be oriented in a pularlity of orientations before being fixed to the stem, wherein the connection portion comprises at least one argument having a first curved surface geometry that substantially comforms to and is matingly engaged with a second curved surface geometry defined by an external outer surface of the acteabular component to selectively orient and position the acteabular component relative to the stem, wherein the stem is rigidly engaged in abutment against an external surface of the at least on augment opposite the first curved surface geometry, and wherein the connection portion and the stem are engaged to one another by a taper lock.

7. The acetabular prosthetic device of claim 6, wherein the at least on augment includes a male tapered portion positioned within a female tapered portion defined by the stem to rigidly interconnect the augment and the stem.

8. An acetabular prosthetic device for implantation in an iliac canal and acetabulum of an ilium, comprising:
    a stem configured to be implanted in the iliac canal; and
    an acetabular component configured to be implanted in the acetabulum and fixed to the stem, the acetabular component further comprising a connection portion to adjustably connect the acetabular component to the stem such that the acetabular component is configured to be oriented in a plurality of orientations before being fixed to the stem;
    wherein the connection portion and the stem are engaged to one another by a taper lock, and wherein the connection portion and the stem are rigidly fixed to one another by a screw extending through an opening in the connection portion and threadedly engaged within a threaded opening in the stem.

9. An acetabular prosthetic device for implantation in an iliac canal and acetabulum of an ilium, comprising:
    a stem component including a shank portion configured to be implanted in the iliac canal;
    an acetabular outer shell component configured to be implanted in the acetabulum, the acetabular outer shell component including an external outer bone bearing surface; and
    a connection component structured to adjustably connect the acetabular outer shell component to the stem component wherein an orientation of the acetabular outer shell component is adjustable to a plurality of orientations relative to the stem component prior to fixation of the acetabular outer shell component at a select orientation relative to the stem component, wherein the connection component has a first curved surface geometry that substantially conforms to and is matingly engaged with a second curved surface geometry defined by the external outer bone bearing surface of the acetabular outer shell component to selectively orient and position the acetabular outer shell component relative to the stem component, wherein the stem component is rigidly engaged in abutment against an external surface of the connection component opposite the first curved surface geometry, wherein the first curved surface geometry of the connection component is rigidly engaged in abutment against the external outer bone bearing surface of the acetabular outer shell component to fix the acetabular outer shell component at a select orientation and position relative to the stem component, and wherein the external outer bone bearing surface of the acetabular outer shell component comprises a porous surface configured to promote bone ingrowth into the acetabular outer shell component.

10. The acetabular prosthetic device of claim 9, wherein the connection component comprises at least one augment positioned between the stem component and the acetabular outer shell component, a first geometric surface of the at least one augment positioned in engagement with a corresponding geometric surface of the stem component to orient the at least one augment with respect to the stem component.

11. The acetabular prosthetic device of claim 10, wherein the first geometric surface of the augment and the corresponding geometric surface of the stem component together define a taper lock.

12. The acetabular prosthetic device of claim 10, wherein the first curved surface geometry of the connection component and the second curved surface geometry defined by the external outer surface of the acetabular outer shell component comprise spherical-shaped surfaces.

13. The acetabular prosthetic device of claim 10, wherein the augment is rigidly fixed in position relative to the stem component by a screw extending through an opening in the augment and threadedly engaged within a threaded opening in the stem component.

14. The acetabular prosthetic device of claim 10, further comprising a number of bone fixation elements extending from a lower surface of the augment and configured for engagement with bone to fix the augment to the bone.

15. The acetabular prosthetic device of claim 10, further comprising a spacer configured to be received between the augment and the acetabular outer shell component, wherein the spacer fills a bone void between the augment and the acetabular outer shell component.

16. The acetabular prosthetic device of claim 9, wherein the connection component is a modular structure comprising a plurality of augments positioned between the stem component and the acetabular outer shell component, a first of the augments including a first geometric surface positioned in engagement with a corresponding geometric surface of the stem component to orient the first augment relative to the stem component, a second of the augments defining the first curved surface geometry positioned in engagement with the second curved surface geometry defined by the external outer bone bearing surface of the acetabular outer shell component to orient the acetabular outer shell component at variable orientations and circumferential positions relative to the stem component.

17. The acetabular prosthetic device of claim 16, wherein the first geometric surface of the first augment and the corresponding geometric surface of the stem component together define a taper lock.

18. The acetabular prosthetic device of claim 16, wherein the first curved surface geometry of the second augment and the second curved surface geometry defined by the external outer bone bearing surface of the acetabular outer shell component comprise spherical-shaped surfaces.

19. The acetabular prosthetic device of claim 16, wherein the first and second augments include mating spherical-shaped surfaces.

20. The acetabular prosthetic device of claim 16, wherein the first and second augments are rigidly fixed to the stem component by a screw extending through an opening in the first and second augments and threadedly engaged within a threaded opening in the stem.

21. The acetabular prosthetic device of claim 9, wherein the first curved surface geometry of the connection component is fixedly engaged with the second curved surface geometry defined by the external outer bone bearing surface of the acetabular outer shell component by bone cement.

22. The acetabular prosthetic device of claim 9, wherein a first geometric surface of the connection component is positioned in engagement with a corresponding geometric surface of the stem component to orient the connection component at a fixed position relative to the stem component.

23. The acetabular prosthetic device of claim 22, wherein the first curved surface geometry of the connection component and the second curved surface geometry defined by the external outer bone bearing surface of the acetabular outer shell component comprise spherical-shaped surfaces.

24. The acetabular prosthetic device of claim 9, wherein the connection component is locked in a fixed orientation and in a rigidly fixed position relative to the stem component by a screw extending through an opening in the connection component and threadedly engaged within a threaded opening in the stem component.

25. The acetabular prosthetic device of claim 9, wherein the connection component is a modular structure comprising a plurality of augments positioned between the stem component and the acetabular outer shell component.

26. The acetabular prosthetic device of claim 9, wherein the first curved surface geometry of the connection component is a concave surface and the second curved surface geometry defined by the external outer bone bearing surface of the acetabular outer shell component is a convex surface, and wherein the concave surface of the connection component is fixedly engaged with the convex surface of the acetabular outer shell component by bone cement.

27. The acetabular prosthetic device of claim 9, wherein the first curved surface geometry of the connection component is selectively engaged with the second curved surface geometry defined by the external outer bone bearing surface of the acetabular outer shell component in an infinite number of circumferential positions along the external outer bone bearing surface of the acetabular outer shell component.

28. An acetabular prosthetic device for implantation in an iliac canal and acetabulum of an ilium, comprising:
a stem component including a shank portion configured to be implanted in the iliac canal;
an acetabular shell component configured to be implanted in the acetabulum; and
a connection component structured to adjustably connect the acetabular shell component to the stem component wherein an orientation of the acetabular shell component is adjustable to a plurality of orientations relative to the stem component prior to fixation of the acetabular shell component at a select orientation relative to the stem component, wherein the connection component has a first curved surface geometry that substantially conforms to and is matingly engaged with a second curved surface geometry defined by an external outer surface of the acetabular shell component to selectively orient and position the acetabular shell component relative to the stem component, wherein the stem component is rigidly engaged in abutment against an external surface of the connection component opposite the first curved surface geometry, and wherein the connection component and the stem component are engaged to one another by a taper lock.

* * * * *